US008758396B2

(12) United States Patent
Ginn et al.

(10) Patent No.: US 8,758,396 B2
(45) Date of Patent: Jun. 24, 2014

(54) VASCULAR SHEATH WITH BIOABSORBABLE PUNCTURE SITE CLOSURE APPARATUS AND METHODS OF USE

(75) Inventors: Richard S. Ginn, San Jose, CA (US); William N. Aldrich, Napa, CA (US)

(73) Assignee: Integrated Vascular Systems, Inc., Sunnyvale, CA (US)

( * ) Notice: Subject to any disclaimer, the term of this patent is extended or adjusted under 35 U.S.C. 154(b) by 0 days.

(21) Appl. No.: 11/411,925

(22) Filed: Apr. 27, 2006

(65) Prior Publication Data

US 2006/0195124 A1 Aug. 31, 2006

Related U.S. Application Data

(63) Continuation of application No. 10/264,306, filed on Oct. 3, 2002, now Pat. No. 7,901,428, which is a continuation of application No. 09/546,998, filed on Apr. 11, 2000, now Pat. No. 6,461,364, which is a continuation-in-part of application No. 09/478,179, filed on Jan. 5, 2000, now Pat. No. 6,197,042.

(51) Int. Cl.
*A61D 1/00* (2006.01)

(52) U.S. Cl.
USPC ............................ 606/213; 606/142; 606/219

(58) Field of Classification Search
USPC .......... 606/153, 139, 142, 213, 215, 216, 219
See application file for complete search history.

(56) References Cited

U.S. PATENT DOCUMENTS

| 287,046 | A | 10/1883 | Norton |
|---|---|---|---|
| 438,400 | A | 10/1890 | Brennen |
| 556,082 | A | 3/1896 | Boeddinghaus |
| 1,088,393 | A | 2/1914 | Backus |
| 1,242,139 | A | 10/1917 | Callahan |
| 1,331,401 | A | 2/1920 | Summers |
| 1,426,111 | A | 8/1922 | Sacker |
| 1,480,935 | A | 1/1924 | Gleason |
| 1,516,990 | A | 11/1924 | Silverman |

(Continued)

FOREIGN PATENT DOCUMENTS

| AU | 2003297432 | 12/2003 |
|---|---|---|
| CA | 2 339 060 | 2/2000 |

(Continued)

OTHER PUBLICATIONS

2006/0144479, Office Action, Mail Date Oct. 16, 2007.
Stretch Comb by Scunci, retrieved via internet at www.scunci.com/productdetail by examiner on Oct. 9, 2007, publication date unavailable.

(Continued)

*Primary Examiner* — Dianne Dornbusch
(74) *Attorney, Agent, or Firm* — Workman Nydegger; Randy Shen

(57) ABSTRACT

Apparatus and methods are provided for use in sealing a vascular puncture site. The invention comprises an introducer sheath with an integrated closure component. The closure component includes a fastener and an advanceable, deformable clip having a delivery configuration in which opposing sides do not contact one another, and a deployed configuration, in which the fastener causes opposing sides of the deformable clip to close towards one another. The clip is advanced along the sheath until it pierces opposing sides of a vessel wall at a puncture site. The clip is then deformed with the fastener to draw opposing sides of the puncture together, and the sheath is withdrawn to seal the wound. The clip and fastener preferably are bioabsorbable.

24 Claims, 4 Drawing Sheets

(56) References Cited

U.S. PATENT DOCUMENTS

| | | |
|---|---|---|
| 1,596,004 A | 8/1926 | De Bengoa |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,108,206 A | 2/1938 | Meeker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,610,631 A | 9/1952 | Calicchio |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,682,180 A | 8/1972 | McFarlane |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,814,104 A | 6/1974 | Irnich et al. |
| 3,823,719 A | 7/1974 | Cummings |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,960,147 A | 6/1976 | Murray |
| 3,976,079 A | 8/1976 | Samuels et al. |
| 3,985,138 A | 10/1976 | Jarvik |
| 4,007,743 A | 2/1977 | Blake |
| 4,011,872 A | 3/1977 | Komiya |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,830,002 A | 5/1989 | Semm |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |

(56) References Cited

U.S. PATENT DOCUMENTS

| | | |
|---|---|---|
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,158,566 A | 10/1992 | Pianetti |
| 5,160,339 A | 11/1992 | Chen et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,176,648 A | 1/1993 | Holmes et al. |
| 5,176,682 A | 1/1993 | Chow |
| 5,176,691 A | 1/1993 | Pierce |
| 5,192,287 A | 3/1993 | Fournier et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,203,787 A | 4/1993 | Noblitt et al. |
| 5,207,697 A | 5/1993 | Carusillo et al. |
| 5,209,756 A | 5/1993 | Seedhorm et al. |
| 5,217,024 A | 6/1993 | Dorsey et al. |
| 5,217,471 A | 6/1993 | Burkhart |
| 5,219,359 A | 6/1993 | McQuilkin et al. |
| 5,222,974 A | 6/1993 | Kensey et al. |
| 5,226,908 A | 7/1993 | Yoon |
| 5,234,449 A | 8/1993 | Bruker et al. |
| 5,236,435 A | 8/1993 | Sewell, Jr. |
| 5,236,445 A | 8/1993 | Hayhurst et al. |
| 5,237,996 A | 8/1993 | Waldman |
| 5,242,456 A | 9/1993 | Nash et al. |
| 5,242,457 A | 9/1993 | Akopov et al. |
| 5,242,459 A | 9/1993 | Buelna |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,258,015 A | 11/1993 | Li et al. |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,282,832 A | 2/1994 | Toso et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,306,280 A | 4/1994 | Bregen et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,442 A | 7/1994 | Green et al. |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,376,101 A | 12/1994 | Green et al. |
| 5,383,896 A | 1/1995 | Gershony et al. |
| 5,383,897 A * | 1/1995 | Wholey ............... 606/213 |
| 5,383,905 A | 1/1995 | Golds et al. |
| RE34,866 E | 2/1995 | Kensey et al. |
| 5,391,173 A | 2/1995 | Wilk |
| 5,392,978 A | 2/1995 | Velez |
| 5,395,030 A | 3/1995 | Kuramoto et al. |
| 5,403,330 A | 4/1995 | Tuason |
| 5,403,331 A | 4/1995 | Chesterfield et al. |
| 5,404,621 A | 4/1995 | Heinke |
| 5,409,499 A | 4/1995 | Yi |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,558 A | 10/1995 | Kolesa et al. |

(56) References Cited

U.S. PATENT DOCUMENTS

| | | | |
|---|---|---|---|
| 5,462,561 A | 10/1995 | Voda | |
| 5,464,413 A | 11/1995 | Siska, Jr. et al. | |
| 5,466,241 A | 11/1995 | Leroy et al. | |
| 5,470,010 A | 11/1995 | Rothfuss et al. | |
| 5,471,982 A | 12/1995 | Edwards et al. | |
| 5,474,557 A | 12/1995 | Mai | |
| 5,474,569 A | 12/1995 | Zinreich et al. | |
| 5,474,572 A | 12/1995 | Hayhurst | |
| 5,476,505 A | 12/1995 | Limon | |
| 5,478,352 A | 12/1995 | Fowler | |
| 5,478,353 A | 12/1995 | Yoon et al. | |
| 5,478,354 A | 12/1995 | Tovey et al. | |
| 5,486,195 A | 1/1996 | Myers et al. | |
| 5,492,119 A | 2/1996 | Abrams | |
| 5,497,933 A | 3/1996 | DeFonzo et al. | |
| 5,501,698 A | 3/1996 | Roth et al. | |
| 5,507,744 A | 4/1996 | Tay et al. | |
| 5,507,755 A | 4/1996 | Gresl et al. | |
| 5,514,159 A | 5/1996 | Matula et al. | |
| 5,521,184 A | 5/1996 | Zimmermann | |
| 5,522,840 A | 6/1996 | Krajicek | |
| 5,527,322 A | 6/1996 | Klein et al. | |
| 5,536,251 A | 7/1996 | Evard et al. | |
| 5,536,267 A | 7/1996 | Edwards | |
| 5,540,712 A | 7/1996 | Kleshinski et al. | |
| 5,540,716 A | 7/1996 | Hlavacek | |
| 5,543,520 A | 8/1996 | Zimmermann | |
| 5,544,802 A | 8/1996 | Crainich | |
| 5,547,474 A | 8/1996 | Kloeckl et al. | |
| 5,560,532 A | 10/1996 | DeFonzo et al. | |
| 5,562,684 A | 10/1996 | Kammerer | |
| 5,571,120 A | 11/1996 | Yoon | |
| 5,573,540 A | 11/1996 | Yoon | |
| 5,573,784 A | 11/1996 | Badylak et al. | |
| 5,575,771 A | 11/1996 | Walinsky | |
| 5,582,616 A | 12/1996 | Bolduc et al. | |
| 5,584,879 A | 12/1996 | Reimold et al. | |
| 5,591,205 A | 1/1997 | Fowler | |
| 5,593,412 A | 1/1997 | Martinez | |
| 5,593,422 A | 1/1997 | Muijs Van der Moer et al. | |
| 5,593,425 A | 1/1997 | Bonutti et al. | |
| 5,601,602 A | 2/1997 | Fowler | |
| 5,609,597 A | 3/1997 | Lehrer | |
| 5,611,986 A | 3/1997 | Datta et al. | |
| 5,613,974 A | 3/1997 | Andreas et al. | |
| 5,613,975 A | 3/1997 | Christy | |
| 5,618,291 A | 4/1997 | Thompson et al. | |
| 5,618,306 A | 4/1997 | Roth et al. | |
| 5,620,452 A | 4/1997 | Yoon | |
| 5,620,461 A | 4/1997 | Muijs et al. | |
| 5,626,614 A | 5/1997 | Hart | |
| 5,630,824 A | 5/1997 | Hart | |
| 5,634,936 A | 6/1997 | Linden et al. | |
| 5,643,318 A | 7/1997 | Tsukernik et al. | |
| 5,645,553 A | 7/1997 | Kolesa et al. | |
| 5,645,565 A | 7/1997 | Rudd et al. | |
| 5,645,566 A | 7/1997 | Brenneman et al. | |
| 5,645,567 A | 7/1997 | Crainich | |
| 5,647,372 A | 7/1997 | Tovey et al. | |
| 5,649,959 A | 7/1997 | Hannam et al. | |
| D383,539 S | 9/1997 | Croley | |
| 5,669,917 A | 9/1997 | Sauer et al. | |
| 5,669,935 A | 9/1997 | Rosenman et al. | |
| 5,672,174 A | 9/1997 | Gough et al. | |
| 5,674,231 A * | 10/1997 | Green et al. | 606/142 |
| 5,676,689 A | 10/1997 | Kensey et al. | |
| 5,676,974 A | 10/1997 | Valdes et al. | |
| 5,681,280 A | 10/1997 | Rusk et al. | |
| 5,681,334 A | 10/1997 | Evans et al. | |
| 5,681,351 A | 10/1997 | Jamiolkowski et al. | |
| 5,683,405 A | 11/1997 | Yacoubian et al. | |
| 5,690,674 A | 11/1997 | Diaz | |
| 5,693,061 A | 12/1997 | Pierce et al. | |
| 5,695,504 A * | 12/1997 | Gifford et al. | 606/153 |
| 5,695,505 A | 12/1997 | Yoon | |
| 5,695,524 A | 12/1997 | Kelley et al. | |
| 5,700,273 A | 12/1997 | Buelna et al. | |
| 5,709,224 A | 1/1998 | Behl et al. | |
| 5,709,708 A | 1/1998 | Thal | |
| 5,713,899 A | 2/1998 | Marnay et al. | |
| 5,715,987 A | 2/1998 | Kelley et al. | |
| 5,716,375 A | 2/1998 | Fowler | |
| 5,720,755 A | 2/1998 | Dakov | |
| 5,720,765 A | 2/1998 | Thal | |
| 5,725,498 A | 3/1998 | Janzen et al. | |
| 5,725,552 A | 3/1998 | Kotula et al. | |
| 5,725,554 A | 3/1998 | Simon et al. | |
| 5,725,556 A | 3/1998 | Moser et al. | |
| 5,728,109 A | 3/1998 | Schulze et al. | |
| 5,728,110 A | 3/1998 | Vidal et al. | |
| 5,728,114 A | 3/1998 | Evans et al. | |
| 5,728,116 A | 3/1998 | Rosenman | |
| 5,728,122 A | 3/1998 | Leschinsky et al. | |
| 5,728,132 A | 3/1998 | Van Tassel et al. | |
| 5,728,133 A | 3/1998 | Kontos | |
| 5,728,143 A | 3/1998 | Gough et al. | |
| 5,732,872 A | 3/1998 | Bolduc et al. | |
| 5,735,736 A | 4/1998 | Volk | |
| 5,735,873 A | 4/1998 | MacLean | |
| 5,735,875 A | 4/1998 | Bonutti et al. | |
| 5,735,877 A | 4/1998 | Pagedas | |
| 5,749,826 A | 5/1998 | Faulkner | |
| 5,749,898 A | 5/1998 | Schulze et al. | |
| 5,752,966 A | 5/1998 | Chang | |
| 5,755,726 A | 5/1998 | Pratt et al. | |
| 5,755,778 A | 5/1998 | Kleshinski | |
| 5,759,189 A | 6/1998 | Ferragamo et al. | |
| 5,766,217 A | 6/1998 | Christy | |
| 5,766,246 A | 6/1998 | Mulhauser et al. | |
| 5,769,862 A | 6/1998 | Kammerer et al. | |
| 5,769,870 A | 6/1998 | Salahieh et al. | |
| 5,776,147 A | 7/1998 | Dolendo | |
| 5,776,150 A | 7/1998 | Nolan et al. | |
| 5,779,707 A | 7/1998 | Bertholet et al. | |
| 5,780,807 A | 7/1998 | Saunders | |
| 5,782,844 A | 7/1998 | Yoon et al. | |
| 5,782,860 A | 7/1998 | Epstein et al. | |
| 5,782,861 A | 7/1998 | Cragg et al. | |
| 5,782,864 A | 7/1998 | Lizardi | |
| 5,795,958 A | 8/1998 | Rao et al. | |
| 5,797,928 A | 8/1998 | Kogasaka | |
| 5,797,929 A | 8/1998 | Andreas et al. | |
| 5,797,931 A | 8/1998 | Bito et al. | |
| 5,797,933 A | 8/1998 | Snow et al. | |
| 5,797,958 A | 8/1998 | Yoon | |
| 5,797,960 A | 8/1998 | Stevens et al. | |
| 5,810,776 A | 9/1998 | Bacich et al. | |
| 5,810,846 A | 9/1998 | Virnich et al. | |
| 5,810,851 A | 9/1998 | Yoon | |
| 5,810,877 A | 9/1998 | Roth et al. | |
| 5,814,069 A | 9/1998 | Schulze et al. | |
| 5,817,113 A | 10/1998 | Gifford, III et al. | |
| 5,820,631 A | 10/1998 | Nobles | |
| 5,827,298 A | 10/1998 | Hart et al. | |
| 5,830,125 A | 11/1998 | Scribner et al. | |
| 5,830,221 A | 11/1998 | Stein et al. | |
| 5,833,698 A | 11/1998 | Hinchliffe et al. | |
| 5,843,167 A | 12/1998 | Dwyer et al. | |
| 5,845,657 A | 12/1998 | Carberry et al. | |
| 5,846,254 A | 12/1998 | Schulze et al. | |
| 5,853,421 A | 12/1998 | Leschinsky et al. | |
| 5,853,422 A | 12/1998 | Huebsch et al. | |
| 5,855,312 A | 1/1999 | Toledano | |
| 5,855,576 A | 1/1999 | LeVeen et al. | |
| 5,858,082 A | 1/1999 | Cruz et al. | |
| 5,860,991 A | 1/1999 | Klein et al. | |
| 5,861,003 A | 1/1999 | Latson et al. | |
| 5,861,005 A | 1/1999 | Kontos | |
| 5,868,755 A | 2/1999 | Kanner et al. | |
| 5,868,762 A | 2/1999 | Cragg et al. | |
| 5,868,763 A | 2/1999 | Spence et al. | |
| 5,871,474 A | 2/1999 | Hermann et al. | |
| 5,871,490 A | 2/1999 | Schulze et al. | |
| 5,871,501 A | 2/1999 | Leschinsky et al. | |

(56) References Cited

U.S. PATENT DOCUMENTS

| | | |
|---|---|---|
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,547 A | 9/1999 | Gough et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,976,159 A | 11/1999 | Bolduc et al. |
| 5,976,161 A | 11/1999 | Kirsch et al. |
| 5,976,174 A | 11/1999 | Ruiz |
| 5,980,517 A | 11/1999 | Gough et al. |
| 5,984,934 A | 11/1999 | Ashby et al. |
| 5,984,948 A | 11/1999 | Hasson |
| 5,984,949 A | 11/1999 | Levin |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,747 A | 2/2000 | Kontos |
| 6,024,750 A | 2/2000 | Mastri |
| 6,024,756 A | 2/2000 | Huebsch et al. |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,066,160 A | 5/2000 | Colvin et al. |
| 6,068,603 A | 5/2000 | Suzuki |
| 6,071,300 A | 6/2000 | Brenneman et al. |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,086,608 A | 7/2000 | Ek et al. |
| 6,090,130 A | 7/2000 | Nash et al. |
| 6,092,561 A | 7/2000 | Schmid |
| 6,095,155 A | 8/2000 | Criscuolo |
| 6,099,553 A | 8/2000 | Hart et al. |
| 6,102,271 A | 8/2000 | Longo et al. |
| 6,106,545 A | 8/2000 | Egan |
| 6,110,184 A * | 8/2000 | Weadock ..................... 606/144 |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,513 A | 9/2000 | Bailey et al. |
| 6,120,524 A | 9/2000 | Taheri |
| 6,126,675 A | 10/2000 | Schervinsky et al. |
| 6,126,677 A | 10/2000 | Ganaja et al. |
| 6,136,010 A | 10/2000 | Modesitt et al. |
| 6,143,004 A | 11/2000 | Davis |
| 6,143,017 A | 11/2000 | Thal |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,174,324 B1 | 1/2001 | Egan et al. |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 | 4/2001 | Fleenor |
| 6,221,102 B1 | 4/2001 | Baker et al. |
| 6,231,561 B1 | 5/2001 | Frazier et al. |
| 6,231,592 B1 | 5/2001 | Bonutti et al. |
| 6,245,079 B1 | 6/2001 | Nobles et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,306,081 B1 | 10/2001 | Ishikawa et al. |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |

(56) References Cited

U.S. PATENT DOCUMENTS

| | | |
|---|---|---|
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,461,366 B1 | 10/2002 | Seguin |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,498 B1 | 2/2003 | Burbank et al. |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,159 B1 | 5/2003 | Edwards et al. |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,051 B2 | 2/2004 | Nakada et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 | 6/2004 | Dana et al. |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,048,747 B2 | 5/2006 | Arcia et al. |
| 7,060,084 B1 | 6/2006 | Loshakove et al. |
| 7,063,661 B2 | 6/2006 | Okada |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,122,002 B2 | 10/2006 | Okada |
| 7,144,411 B2 | 12/2006 | Ginn et al. |
| 7,147,646 B2 | 12/2006 | Dana et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,229,452 B2 | 6/2007 | Kayan |
| 7,261,716 B2 | 8/2007 | Strobel et al. |
| 7,270,672 B1 | 9/2007 | Singer |
| 7,306,614 B2 | 12/2007 | Weller et al. |

(56) References Cited

U.S. PATENT DOCUMENTS

| | | |
|---|---|---|
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,507,200 B2 | 3/2009 | Okada |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,727,249 B2 | 6/2010 | Rahmani |
| 7,731,655 B2 | 6/2010 | Smith et al. |
| 7,749,249 B2 | 7/2010 | Gelbart et al. |
| 7,780,696 B2 | 8/2010 | Daniel et al. |
| 7,799,042 B2 | 9/2010 | Williamson, IV et al. |
| 7,819,895 B2 | 10/2010 | Ginn et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2001/0053909 A1 | 12/2001 | Nakada |
| 2002/0022822 A1 | 2/2002 | Cragg et al. |
| 2002/0026208 A1 | 2/2002 | Belef et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049472 A1 | 4/2002 | Coleman et al. |
| 2002/0058960 A1 | 5/2002 | Hudson et al. |
| 2002/0062104 A1 | 5/2002 | Ashby et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0188275 A1 | 12/2002 | McGuckin et al. |
| 2002/0193808 A1 | 12/2002 | Belef et al. |
| 2002/0198562 A1 | 12/2002 | Ackerfeldt et al. |
| 2002/0198589 A1 | 12/2002 | Leong |
| 2003/0004543 A1* | 1/2003 | Gleeson et al. ............... 606/213 |
| 2003/0009180 A1 | 1/2003 | Hinchliffe et al. |
| 2003/0009196 A1 | 1/2003 | Peterson |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |

(56) References Cited

U.S. PATENT DOCUMENTS

| | | |
|---|---|---|
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0256532 A1 | 11/2005 | Nayak et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0265012 A1 | 11/2006 | Anderson |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0083230 A1 | 4/2007 | Javois |
| 2007/0083231 A1 | 4/2007 | Lee |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0287967 A1 | 11/2008 | Andreas et al. |
| 2008/0287988 A1 | 11/2008 | Smith et al. |
| 2008/0300628 A1 | 12/2008 | Ellingwood |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0066163 A1 | 3/2011 | Cho et al. |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Karineimi et al. |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |
| 2013/0338708 A1 | 12/2013 | Cummins et al. |

FOREIGN PATENT DOCUMENTS

| | | |
|---|---|---|
| DE | 197 11 288 | 1/1998 |
| DE | 297 23 736 U 1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |

(56) References Cited

FOREIGN PATENT DOCUMENTS

| | | |
|---|---|---|
| GB | 1 358 466 | 7/1974 |
| GB | 2 075 144 | 11/1981 |
| GB | 2 397 240 | 7/2004 |
| IE | S 2000/0722 | 10/2001 |
| IE | S 2000/0724 | 10/2001 |
| IE | S 2001/0547 | 7/2002 |
| IE | S 2001/0815 | 7/2002 |
| IE | S 2001/0748 | 8/2002 |
| IE | S 2001/0749 | 8/2002 |
| IE | S 2002/0452 | 12/2002 |
| IE | S 2002/0664 | 2/2003 |
| IE | S 2002/0665 | 2/2003 |
| IE | S 2002/0451 | 7/2003 |
| IE | S 2002/0552 | 7/2003 |
| IE | S 2003/0424 | 12/2003 |
| IE | S 2003/0490 | 1/2004 |
| IE | S 2004/0368 | 11/2005 |
| IE | S 2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 20010527 | 1/2001 |
| ZA | 200100528 | 1/2001 |

OTHER PUBLICATIONS

U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
Database WPI; Section PQ, Week 200120; Derwent Publications Ltd., London GB; AN 2001-203165; XP002199926 & ZA 200 100 528 A (Anthony T), Feb. 28, 2001 abstract.
2002/0072768, Office Action, Mail Date Aug. 27, 2004.
2002/0072768, Office Action, Mail Date Feb. 23, 2005.
2002/0072768, Office Action, Mail Date Apr. 11, 2005.
2002/0072768, Office Action, Mail Date Jul. 27, 2005.
2002/0072768, Office Action, Mail Date Mar. 6, 2006.
2002/0072768, Office Action, Mail Date May 24, 2006.
2002/0072768, Office Action, Mail Date Oct. 26, 2006.
2002/0072768, Office Action, Mail Date Apr. 19, 2007.
2002/0133193, Office Action, Mail Date Nov. 4, 2004.
2002/0133193, Office Action, Mail Date May 4, 2005.
2002/0133193, Office Action, Mail Date Oct. 18, 2005.
2002/0133193, Notice of Allowance, Mail Date Apr. 18, 2007.
2002/0133193, Notice of Allowance, Mail Date Sep. 27, 2007.
2003/0078598, Office Action, Mail Date Feb. 9, 2005.
2003/0078598, Office Action, Mail Date May 26, 2005.
2003/0078598, Office Action, Mail Date Oct. 4, 2005.
2003/0078598, Notice of Allowance, Mail Date May 10, 2006.

(56) References Cited

OTHER PUBLICATIONS

2003/0078598, Notice of Allowance, Mail Date Jul. 2, 2007.
2003/0195561, Office Action, Mail Date Jun. 10, 2004.
2003/0195561, Notice of Allowance, Mail Date Sep. 21, 2004.
2003/0195561, Office Action, Mail Date Jan. 3, 2006.
2003/0195561, Issue Notification, Mail Date Feb. 15, 2006.
2003/0195561, Office Action, Mail Date May 16, 2006.
2003/0195561, Notice of Allowance, Mail Date Dec. 28, 2006.
2003/0195561, Notice of Allowance, Mail Date Jul. 10, 2007.
2003/0195561, Notice of Allowance, Mail Date Aug. 2, 2007.
2004/0153123, Office Action, Mail Date Sep. 22, 2006.
2004/0153123, Office Action, Mail Date Jan. 31, 2007.
2004/0153123, Office Action, Mail Date Sep. 18, 2007.
2004/0153122, Office Action, Mail Date Nov. 30, 2005.
2004/0153122, Office Action, Mail Date Aug. 23, 2006.
2004/0153122, Office Action, Mail Date Feb. 13, 2007.
2004/0153122, Office Action, Mail Date Sep. 12, 2007.
2004/0073255, Office Action, Mail Date Sep. 15, 2006.
2004/0073255, Office Action, Mail Date Apr. 18, 2007.
2004/0073236, Office Action, Mail Date Sep. 19, 2006.
2004/0073236, Office Action, Mail Date May 2, 2007.
2004/0009289, Office Action, Mail Date Jun. 30, 2006.
2004/0009289, Office Action, Mail Date Oct. 20, 2006.
2004/0009289, Office Action, Mail Date May 29, 2007.
2004/0167570, Office Action, Mail Date Oct. 30, 2006.
2004/0167570, Office Action, Mail Date Apr. 17, 2007.
2004/0167570, Office Action, Mail Date Aug. 31, 2007.
2005/0274768, Office Action, Mail Date Oct. 19, 2006.
2005/0274768, Office Action, Mail Date Aug. 10, 2007.
2005/0216057, Office Action, Mail Date Feb. 6, 2007.
2005/0216057, Office Action, Mail Date May 30, 2007.
2005/0234508, Office Action, Mail Date Aug. 13, 2007.
2006/0135989, Office Action, Mail Date Nov. 30, 2006.
2006/0135989, Office Action, Mail Date Sep. 5, 2007.
2006/0195123, Office Action, Mail Date May 14, 2007.
6,197,042, Notice of Allowance, Mail Date Nov. 6, 2000.
6,197,042, Issue Notification, Mail Date Feb. 15, 2001.
6,277,140, Office Action, Mail Date Mar. 26, 2001.
6,277,140, Notice of Allowance, Mail Date Jun. 4, 2001.
6,277,140, Issue Notification, Mail Date Aug. 6, 2001.
6,391,048, Notice of Allowance, Mail Date Mar. 26, 2001.
6,391,048, Office Action, Mail Date Sep. 5, 2001.
6,391,048, Notice of Allowance, Mail Date Feb. 11, 2002.
6,391,048, Issue Notification, Mail Date May 3, 2002.
6,461,364, Notice of Allowance, Mail Date May 6, 2002.
6,461,364, Issue Notification, Mail Date Sep. 19, 2002.
6,582,452, Notice of Allowance, Mail Date Jan. 31, 2003.
6,582,452, Issue Notification, Mail Date Jun. 5, 2003.
6,616,686, Office Action, Mail Date Dec. 17, 2002.
6,616,686, Notice of Allowance, Mail Date Apr. 21, 2003.
6,616,686, Issue Notification, Mail Date Aug. 21, 2003.
6,623,510, Notice of Allowance, Mail Date Apr. 11, 2003.
6,623,510, Office Action, Mail Date Jun. 9, 2003.
6,623,510, Issue Notification, Mail Date Sep. 4, 2003.
6,632,238, Office Action, Mail Date Feb. 26, 2003.
6,632,238, Notice of Allowance, Mail Date Jun. 16, 2003.
6,632,238, Issue Notification, Mail Date Sep. 25, 2003.
6,669,714, Office Action, Mail Date Mar. 4, 2003.
6,669,714, Notice of Allowance, Mail Date Jul. 28, 2003.
6,669,714, Issue Notification, Mail Date Dec. 11, 2003.
6,695,867, Notice of Allowance, Mail Date Sep. 29, 2003.
6,695,867, Issue Notification, Mail Date Feb. 5, 2004.
6,719,777, Office Action, Mail Date Feb. 20, 1987.
6,719,777, Notice of Allowance, Mail Date Jul. 24, 1987.
6,719,777, Issue Notification, Mail Date Mar. 25, 2004.
6,749,621, Notice of Allowance, Mail Date Feb. 9, 2004.
6,749,621, Office Action, Mail Date Apr. 13, 2004.
6,749,621, Issue Notification, Mail Date May 27, 2004.
6,780,197, Office Action, Mail Date Sep. 11, 2003.
6,780,197, Office Action, Mail Date Feb. 9, 2004.
6,780,197, Notice of Allowance, Mail Date Mar. 17, 2004.
6,780,197, Issue Notification, Mail Date Aug. 5, 2004.
6,926,731, Office Action, Mail Date Nov. 16, 2004.
6,926,731, Notice of Allowance, Mail Date Apr. 6, 2005.
6,926,731, Issue Notification, Mail Date Jul. 20, 2005.
6,942,674, Office Action, Mail Date Sep. 29, 2004.
6,942,674, Notice of Allowance, Mail Date May 13, 2005.
6,942,674, Issue Notification, Mail Date Aug. 24, 2005.
7,001,398, Office Action, Mail Date Mar. 22, 2005.
7,001,398, Notice of Allowance, Mail Date Jul. 6, 2005.
7,001,398, Notice of Allowance, Mail Date Oct. 5, 2005.
7,001,398, Issue Notification, Mail Date Feb. 21, 2006.
7,008,435, Office Action, Mail Date Apr. 20, 2005.
7,008,435, Office Action, Mail Date Aug. 10, 2005.
7,008,435, Notice of Allowance, Mail Date Oct. 18, 2005.
7,008,435, Issue Notification, Mail Date Feb. 15, 2006.
7,108,709, Office Action, Mail Date Jul. 27, 2004.
7,108,709, Office Action, Mail Date Dec. 17, 2004.
7,108,709, Notice of Allowance, Mail Date Mar. 9, 2005.
7,108,709, Office Action, Mail Date Aug. 11, 2006.
7,108,709, Issue Notification, Mail Date Aug. 30, 2006.
7,111,768, Office Action, Mail Date Feb. 23, 2006.
7,111,768, Notice of Allowance, Mail Date May 31, 2006.
7,111,768, Issue Notification, Mail Date Sep. 6, 2006.
7,163,551, Office Action, Mail Date Jan. 10, 2006.
7,163,551, Notice of Allowance, Mail Date Sep. 20, 2006.
7,163,551, Issue Notification, Mail Date Dec. 27, 2006.
7,211,101, Office Action, Mail Date Aug. 10, 2005.
7,211,101, Office Action, Mail Date Dec. 19, 2005.
7,211,101, Office Action, Mail Date Apr. 21, 2006.
7,211,101, Notice of Allowance, Mail Date Dec. 27, 2006.
7,211,101, Issue Notification, Mail Date Apr. 11, 2007.
"Hand tool for forming telephone connections—comprises pliers with reciprocably driven ram crimping clip around conductors against anvil", Derwent-ACC-No. 1978-B8090A.
U.S. Appl. No. 10/006,400, Mail Date Apr. 2, 2008, Office Action.
U.S. Appl. No. 10/147,774, Mail Date Feb. 4, 2008, Notice of Allowance.
U.S. Appl. No. 10/264,306, Mail Date May 26, 2005, Office Action.
U.S. Appl. No. 10/264,306, Mail Date Feb. 4, 2008, Notice of Allowance.
U.S. Appl. No. 10/264,306, Mail Date Jun. 27, 2008, Office Action.
U.S. Appl. No. 10/356,214, Mail Date Mar. 6, 2008, Office Action.
U.S. Appl. No. 10/435,104, Mail Date Apr. 4, 2008, Notice of Allowance.
U.S. Appl. No. 10/517,004, Mail Date Jan. 30, 2008, Office Action.
U.S. Appl. No. 10/541,083, Mail Date May 5, 2008, Office Action.
U.S. Appl. No. 10/638,115, Mail Date Feb. 7, 2008, Office Action.
U.S. Appl. No. 10/667,144, Mail Date May 12, 2008, Office Action.
U.S. Appl. No. 10/682,459, Mail Date Apr. 2, 2008, Office Action.
U.S. Appl. No. 10/786,444, Mail Date Apr. 24, 2008, Office Action.
U.S. Appl. No. 10/787,073, Mail Date Feb. 22, 2008, Office Action.
U.S. Appl. No. 11/113,549, Mail Date Apr. 16, 2008, Office Action.
U.S. Appl. No. 11/152,562, Mail Date May 13, 2008, Office Action.
U.S. Appl. No. 11/344,891, Mail Date Apr. 29, 2008, Office Action.
U.S. Appl. No. 11/406,203, Mail Date May 23, 2008, Notice of Allowance.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.

(56) References Cited

OTHER PUBLICATIONS

H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.

Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.

J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.

Jeremy L Gilbert PhD, Wound Closure Biomaterials and Devices, Shock., Mar. 1999, p. 226, vol. 11—No. 3, Institution Northwestern University.

Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.

K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive. org, Jun. 1998, Original Publisher: http://prostar.com, may also be found at http://web.archive.org/web/19980630040429/www. perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 10/147,774, Mail Date Jun. 30, 2008, Office Action.
U.S. Appl. No. 10/435,104, Mail Date Sep. 26, 2008, Notice of Allowance.
U.S. Appl. No. 10/541,083, Mail Date Sep. 19, 2008, Notice of Allowance.
U.S. Appl. No. 10/616,832, Mail Date Sep. 17, 2008, Office Action.
U.S. Appl. No. 10/786,444, Mail Date Oct. 17, 2008, Office Action.
U.S. Appl. No. 11/198,811, Mail Date Aug. 26, 2008, Office Action.
U.S. Appl. No. 11/406,203, Mail Date Sep. 22, 2008, Notice of Allowance.
U.S. Appl. No. 60/696,069, filed Jul. 1, 2005, Pantages et al.
U.S. Appl. No. 60/946,026, filed Jun. 25, 2007, Ellingwood.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
McCarthy, et al., "Tension (Stay) Suture Bridge", J. of International College of Surgeons, 34(5), pp. 613-614 (Nov. 1960).
U.S. Appl. No. 09/680,837, Mail Date Jul. 9, 2002, Office Action.
U.S. Appl. No. 09/680,837, Mail Date Nov. 6, 2002, Office Action.
U.S. Appl. No. 09/680,837, Mail Date Mar. 25, 2003, Office Action.
U.S. Appl. No. 09/680,837, Mail Date Jun. 16, 2003, Notice of Allowance.
U.S. Appl. No. 09/680,837, Mail Date Sep. 11, 2003, Issue Notification.
U.S. Appl. No. 10/006,400, Mail Date Jan. 2, 2009, Office Action.
U.S. Appl. No. 10/147,774, Mail Date Mar. 18, 2009, Office Action.
U.S. Appl. No. 10/264,306, Mail Date Feb. 26, 2009, Office Action.
U.S. Appl. No. 10/305,923, Mail Date Nov. 1, 2004, Office Action.
U.S. Appl. No. 10/305,923, Mail Date Mar. 3, 2005, Notice of Allowance.
U.S. Appl. No. 10/356,214, Mail Date Nov. 4, 2008, Office Action.
U.S. Appl. No. 10/356,214, Mail Date Apr. 29, 2009, Office Action.
U.S. Appl. No. 10/435,104, Mail Date Nov. 14, 2007, Notice of Allowance.
U.S. Appl. No. 10/435,104, Mail Date Dec. 22, 2008, Notice of Allowance.
U.S. Appl. No. 10/517,004, Mail Date Aug. 13, 2008, Notice of Allowance.

(56) References Cited

OTHER PUBLICATIONS

U.S. Appl. No. 10/517,004, Mail Date Feb. 10, 2009, Notice of Allowance.
U.S. Appl. No. 10/541,083, Mail Date Oct. 31, 2007, Office Action.
U.S. Appl. No. 10/541,083, Mail Date Dec. 29, 2008, Notice of Allowance.
U.S. Appl. No. 10/638,115, Mail Date Oct. 29, 2008, Office Action.
U.S. Appl. No. 10/667,144, Mail Date Mar. 24, 2009, Office Action.
U.S. Appl. No. 10/669,313, Mail Date Jan. 11, 2006, Notice of Allowance.
U.S. Appl. No. 10/669,313, Mail Date Jun. 28, 2006, Notice of Allowance.
U.S. Appl. No. 10/669,313, Mail Date Nov. 15, 2006, Issue Notification.
U.S. Appl. No. 10/682,459, Mail Date Dec. 4, 2008, Office Action.
U.S. Appl. No. 10/787,073, Mail Date Nov. 12, 2008, Office Action.
U.S. Appl. No. 10/908,721, Mail Date Nov. 25, 2008, Office Action.
U.S. Appl. No. 11/048,503, Mail Date Mar. 13, 2009, Office Action.
U.S. Appl. No. 11/152,562, Mail Date Feb. 13, 2009, Office Action.
U.S. Appl. No. 11/344,793, Mail Date Jan. 22, 2009, Office Action.
U.S. Appl. No. 11/344,868, Mail Date Mar. 25, 2009, Office Action.
U.S. Appl. No. 11/344,891, Mail Date Dec. 8, 2008, Office Action.
U.S. Appl. No. 11/344,891, Mail Date Feb. 26, 2009, Office Action.
U.S. Appl. No. 11/396,731, Mail Date Feb. 13, 2009, Office Action.
U.S. Appl. No. 11/406,203, Mail Date Mar. 3, 2009, Office Action.
U.S. Appl. No. 11/427,297, Mail Date Jan. 30, 2009, Office Action.
U.S. Appl. No. 11/461,323, Mail Date May 2, 2007, Office Action.
U.S. Appl. No. 11/461,323, Mail Date Oct. 29, 2007, Office Action.
U.S. Appl. No. 11/461,323, Mail Date Apr. 25, 2008, Office Action.
U.S. Appl. No. 11/461,323, Mail Date Nov. 6, 2008, Office Action.
U.S. Appl. No. 11/532,325, Mail Date Feb. 23, 2009, Office Action.
U.S. Appl. No. 11/744,089, Mail Date Nov. 26, 2008, Office Action.
U.S. Appl. No. 12/106,928, Mail Date Jan. 23, 2009, Office Action.
U.S. Appl. No. 12/106,937, Mail Date Mar. 30, 2009, Office Action.
U.S. Appl. No. 29/296,370, Mail Date Aug. 18, 2008, Office Action.
U.S. Appl. No. 29/296,370, Mail Date Dec. 2, 2008, Notice of Allowance.
U.S. Appl. No. 29/296,370, Mail Date Apr. 1, 2009, Notice of Allowance.
U.S. Appl. No. 12/481,377, Mail Date Jan. 3, 2012, Office Action.
U.S. Appl. No. 12/548,274, Mail Date Dec. 28, 2011, Office Action.
U.S. Appl. No. 12/684,562, Mail Date Dec. 28, 2011, Office Action.
U.S. Appl. No. 10/006,400, Mail Date Jul. 9, 2009, Notice of Allowance.
U.S. Appl. No. 10/147,774, Mail Date Oct. 26, 2009, Office Action.
U.S. Appl. No. 10/264,306, Mail Date Aug. 13, 2009, Office Action.
U.S. Appl. No. 10/517,004, Mail Date Jun. 26, 2009, Notice of Allowance.
U.S. Appl. No. 10/541,083, Mail Date Apr. 16, 2009, Notice of Allowance.
U.S. Appl. No. 10/541,083, Mail Date Sep. 30, 2009, Notice of Allowance.
U.S. Appl. No. 10/616,832, Mail Date Jul. 21, 2009, Office Action.
U.S. Appl. No. 10/638,115, Mail Date May 7, 2009, Notice of Allowance.
U.S. Appl. No. 10/667,144, Mail Date Nov. 23, 2009, Office Action.
U.S. Appl. No. 10/682,459, Mail Date Jun. 10, 2009, Office Action.
U.S. Appl. No. 10/786,444, Mail Date Jun. 18, 2009, Office Action.
U.S. Appl. No. 10/787,073, Mail Date Aug. 13, 2009, Office Action.
U.S. Appl. No. 10/908,721, Mail Date Jun. 23, 2009, Office Action.
U.S. Appl. No. 11/048,503, Mail Date Jun. 26, 2009, Office Action.
U.S. Appl. No. 11/113,549, Mail Date Jul. 21, 2009, Office Action.
U.S. Appl. No. 11/152,562, Mail Date Jul. 6, 2009, Office Action.
U.S. Appl. No. 11/198,811, Mail Date Sep. 22, 2009, Office Action.
U.S. Appl. No. 11/344,891, Mail Date Oct. 7, 2009, Office Action.
U.S. Appl. No. 11/390,586, Mail Date Jun. 24, 2009, Office Action.
U.S. Appl. No. 11/396,141, Mail Date May 22, 2009, Restriction Requirement.
U.S. Appl. No. 11/396,141, Mail Date Aug. 26, 2009, Office Action.
U.S. Appl. No. 11/396,731, Mail Date May 22, 2009, Office Action.
U.S. Appl. No. 11/406,203, Mail Date Sep. 16, 2009, Office Action.
U.S. Appl. No. 11/461,323, Mail Date Jul. 27, 2009, Office Action.
U.S. Appl. No. 11/532,325, Mail Date Jun. 17, 2009, Office Action.
U.S. Appl. No. 11/744,089, Mail Date Aug. 14, 2009, Office Action.
U.S. Appl. No. 11/958,295, Mail Date Aug. 27, 2009, Office Action.
U.S. Appl. No. 12/106,937, Mail Date Nov. 18, 2009, Office Action.
U.S. Appl. No. 12/106,928, Mail Date Oct. 5, 2009, Office Action.
U.S. Appl. No. 12/403,256, Mail Date Dec. 16, 2009, Restriction Requirement.
U.S. Appl. No. 11/113,549, Mail Date Jan. 4, 2011, Office Action
U.S. Appl. No. 12/897,358, Mail Date Jan. 12, 2012, Notice of Allowance.
U.S. Appl. No. 12/608,773, Mail Date Jan. 7, 2013, Office Action.
U.S. Appl. No. 13/490,143, Mail Date Jan. 4, 2013, Restriction Requirement.
U.S. Appl. No. 13/615,547, Mail Date Jan. 18, 2013, Office Action.
U.S. Appl. No. 10/435,104, Mail Date Jan. 12, 2011, Issue Notification.
U.S. Appl. No. 12/402,398, Mail Date Jan. 24, 2011, Office Action.
U.S. Appl. No. 12/945,646, Mail Date Jan. 20, 2011, Office Action.
U.S. Appl. No. 12/338,977, Mail Date Jan. 19, 2012, Office Action.
U.S. Appl. No. 12/684,569, Mail Date Jan. 27, 2012, Office Action.
U.S. Appl. No. 11/344,891, Mail Date Jan. 22, 2013, Notice of Allowance.
U.S. Appl. No. 13/030,922, Mail Date Jan. 31, 2013, Office Action.
U.S. Appl. No. 13/153,594, Mail Date Jan. 29, 2013, Office Action.
U.S. Appl. No. 10/616,832, Mail Date Jan. 26, 2011, Issue Notification.
U.S. Appl. No. 11/152,562, Mail Date Jan. 26, 2011, Issue Notification.
U.S. Appl. No. 11/767,818, Mail Date Feb. 3, 2012, Notice of Allowance.
U.S. Appl. No. 12/684,542, Mail Date Jan. 30, 2012, Office Action.
U.S. Appl. No. 12/941,809, Mail Date Jan. 30, 2012, Office Action.
U.S. Appl. No. 12/966,923, Mail Date Feb. 3, 2012, Notice of Allowance.
U.S. Appl. No. 12/961,331, Mail Date Feb. 1, 2013, Office Action.
U.S. Appl. No. 13/488,233, Mail Date Feb. 5, 2013, Notice of Allowance.
U.S. Appl. No. 12/608,769, Mail Date Feb. 10, 2012, Office Action.
U.S. Appl. No. 12/684,400, Mail Date Feb. 13, 2012, Office Action.
U.S. Appl. No. 12/724,304, Mail Date Feb. 10, 2012, Office Action.
U.S. Appl. No. 10/667,144, Mail Date Feb. 15, 2012, Issue Notification.
U.S. Appl. No. 12/135,858, Mail Date Feb. 16, 2012, Office Action.
U.S. Appl. No. 12/684,562, Mail Date Feb. 16, 2012, Office Action.
U.S. Appl. No. 12/945,646, Mail Date Feb. 21, 2012, Notice of Allowance.
U.S. Appl. No. 13/030,922, filed Feb. 18, 2011, Cummins.
U.S. Appl. No. 10/356,214, Mail Date Feb. 23, 2011, Issue Notification.
U.S. Appl. No. 13/039,087, filed Mar. 2, 2011, Palermo et al.
U.S. Appl. No. 11/852,190, Mail Date Mar. 2, 2011, Office Action.
U.S. Appl. No. 12/122,603, Mail Date Mar. 3, 2011, Office Action.
U.S. Appl. No. 11/427,297, Mail Date Sep. 15, 2009, Office Action.
U.S. Appl. No. 11/958,281, Mail Date Mar. 10, 2011, Office Action.
U.S. Appl. No. 11/532,576, Mail Date Mar. 16, 2011, Issue Notification.
U.S. Appl. No. 11/396,731, Mail Date Mar. 22, 2011, Office Action.
U.S. Appl. No. 11/427,297, Mail Date Mar. 21, 2011, Office Action.
U.S. Appl. No. 12/114,031, Mail Date Mar. 6, 2012, Office Action.
U.S. Appl. No. 12/684,470, Mail Date Mar. 23 2012, Office Action.
U.S. Appl. No. 12/688,065, Mail Date Mar. 13, 2012, Office Action.
U.S. Appl. No. 12/897,358, Mail Date Mar. 5, 2012, Notice of Allowance.
U.S. Appl. No. 12/973,204, Mail Date Mar. 7, 2012, Notice of Allowance.
U.S. Appl. No. 12/987,792, Mail Date Mar. 13, 2012, Office Action.
U.S. Appl. No. 12/113,851, Mail Date Mar. 29, 2012, Office Action.
U.S. Appl. No. 12/403,277, Mail Date Apr. 3, 2012, Office Action.
U.S. Appl. No. 10/682,459, Mail Date Apr. 1, 2011, Notice of Allowance.
U.S. Appl. No. 12/403,277, Mail Date Mar. 31, 2011, Office Action.

(56) References Cited

OTHER PUBLICATIONS

U.S. Appl. No. 13/971,829, filed Mar. 8, 2013, Roorda et al.
U.S. Appl. No. 13/791,846, filed Mar. 8, 2013, Palermo.
U.S. Appl. No. 13/112,618, Mail Date Mar. 29, 2013, Office Action.
U.S. Appl. No. 13/112,631, Mail Date Mar. 29, 2013, Office Action.
U.S. Appl. No. 13/308,227, Mail Date Apr. 10, 2013, Office Action.
U.S. Appl. No. 13/525,839, Mail Date Apr. 1, 2013, Office Action.
U.S. Appl. No. 12/114,091, Mail Date Apr. 5, 2012, Office Action.
U.S. Appl. No. 12/684,542, Mail Date Apr. 16, 2012, Office Action.
U.S. Appl. No. 11/744,089, Mail Date Apr. 15, 2013, Office Action.
U.S. Appl. No. 12/850,242, Mail Date Apr. 18, 2013, Office Action.
U.S. Appl. No. 13/052,634, Mail Date Feb. 8, 2013, Office Action.
U.S. Appl. No. 13/052,634, Mail Date Apr. 22, 2013, Office Action.
U.S. Appl. No. 13/615,547, Mail Date Apr. 12, 2013, Notice of Allowance.
U.S. Appl. No. 12/122,603, Mail Date Apr. 22, 2011, Office Action.
U.S. Appl. No. 11/396,141, Mail Date Apr. 30, 2013, Office Action.
U.S. Appl. No. 11/852,190, Mail Date Apr. 24, 2013, Office Action.
U.S. Appl. No. 12/848,642, Mail Date Apr. 26, 2013, Office Action.
U.S. Appl. No. 13/490,143, Mail Date Apr. 29, 2013, Notice of Allowance.
U.S. Appl. No. 12/113,851, Mail Date Apr. 27, 2011, Office Action.
U.S. Appl. No. 12/481,377, Mail Date Apr. 28, 2011, Office Action.
U.S. Appl. No. 12/114,031, Mail Date May 11, 2011, Office Action.
U.S. Appl. No. 12/143,020, Mail Date May 11, 2011, Office Action.
U.S. Appl. No. 11/344,891, Mail Date May 15, 2013, Issue Notification.
U.S. Appl. No. 12/955,859, Mail Date May 16, 2013, Office Action.
U.S. Appl. No. 13/488,233, Mail Date May 15, 2013, Issue Notification.
U.S. Appl. No. 11/390,586, Mail Date May 3, 2012, Notice of Allowance.
U.S. Appl. No. 12/684,400, Mail Date May 9, 2012, Office Action.
U.S. Appl. No. 12/897,358, Mail Date May 2, 2012, Issue Notification.
U.S. Appl. No. 12/966,923, Mail Date May 16, 2012, Issue Notification.
U.S. Appl. No. 13/898,202, filed May 20, 2013, Walberg et al.
U.S. Appl. No. 13/153,594, Mail Date May 29, 2013, Office Action.
U.S. Appl. No. 13/791,829, Mail Date May 29, 2013, Office Action.
U.S. Appl. No. 12/143,020, Mail Date May 30, 2013, Issue Notification.
U.S. Appl. No. 12/393,877, Mail Date May 21, 2012, Office Action.
U.S. Appl. No. 12/941,809, Mail Date Jun. 1, 2012, Office Action.
U.S. Appl. No. 12/945,646, Mail Date May 30, 2012, Issue Notification.
U.S. Appl. No. 12/973,204, Mail Date May 30, 2012, Issue Notification.
U.S. Appl. No. 13/153,594, filed Jun. 6, 2011, Reyes et al.
U.S. Appl. No. 10/667,144, Mail Date Jun. 6, 2011, Office Action.
U.S. Appl. No. 12/608,773, Mail Date Jun. 7, 2012, Office Action.
U.S. Appl. No. 13/026,989, Mail Date Jun. 8, 2012, Office Action.
U.S. Appl. No. 12/338,977, Mail Date Jun. 19, 2013, Office Action.
U.S. Appl. No. 11/344,891, Mail Date Jun. 26, 2013, Issue Notification.
U.S. Appl. No. 12/402,398, Mail Date Jun. 26, 2013, Issue Notification.
U.S. Appl. No. 13/112,631, Mail Date Jun. 26, 2013, Office Action.
U.S. Appl. No. 12/481,377, Mail Date Jun. 21, 2011, Office Action.
U.S. Appl. No. 12/106,928, Mail Date Jun. 28, 2013, Office Action.
U.S. Appl. No. 12/106,937, Mail Date Jun. 28, 2013, Office Action.
U.S. Appl. No. 12/941,809, Mail Date Jul. 3, 2013, Office Action.
U.S. Appl. No. 12/961,331, Mail Date Jul. 3, 2013, Office Action.
U.S. Appl. No. 12/114,091, Mail Date Jul. 7, 2011, Office Action.
U.S. Appl. No. 12/945,646, Mail Date Jul. 6, 2011, Office Action.
U.S. Appl. No. 60/693,531, filed Jun. 24, 2005, Carly.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, Mail Date Apr. 27, 2010, Notice of Allowance.
U.S. Appl. No. 10/147,774, Mail Date Jun. 8, 2010, Office Action.
U.S. Appl. No. 10/264,306, Mail Date Jan. 27, 2010, Office Action.
U.S. Appl. No. 10/264,306, Mail Date Jun. 15, 2010, Office Action.
U.S. Appl. No. 10/356,214, Mail Date Jan. 13, 2010, Notice of Allowance.
U.S. Appl. No. 10/356,214, Mail Date May 13, 2010, Notice of Allowance.
U.S. Appl. No. 10/435,104, Mail Date Jan. 20, 2010, Notice of Allowance.
U.S. Appl. No. 10/435,104, Mail Date Jun. 2, 2010, Office Action.
U.S. Appl. No. 10/517,004, Mail Date Jan. 11, 2010, Notice of Allowance.
U.S. Appl. No. 10/517,004, Mail Date Apr. 23, 2010, Notice of Allowance.
U.S. Appl. No. 10/541,083, Mail Date Feb. 5, 2010, Notice of Allowance.
U.S. Appl. No. 10/541,083, Mail Date May 10, 2010, Notice of Allowance.
U.S. Appl. No. 10/616,832, Mail Date Jan. 11, 2010, Notice of Allowance.
U.S. Appl. No. 10/616,832, Mail Date May 12, 2010, Notice of Allowance.
U.S. Appl. No. 10/638,115, Mail Date Dec. 1, 2009, Notice of Allowance.
U.S. Appl. No. 10/638,115, Mail Date Apr. 2, 2010, Notice of Allowance.
U.S. Appl. No. 10/667,144, Mail Date Jun. 22, 2010, Office Action.
U.S. Appl. No. 10/682,459, Mail Date Dec. 23, 2009, Office Action.
U.S. Appl. No. 10/682,459, Mail Date Apr. 28, 2010, Office Action.
U.S. Appl. No. 10/786,444, Mail Date Jan. 14, 2010, Office Action.
U.S. Appl. No. 10/787,073, Mail Date Feb. 17, 2010, Notice of Allowance.
U.S. Appl. No. 10/908,721, Mail Date Feb. 2, 2010, Office Action.
U.S. Appl. No. 11/048,503, Mail Date Jan. 11, 2010, Notice of Allowance.
U.S. Appl. No. 11/048,503, Mail Date Apr. 26, 2010, Notice of Allowance.
U.S. Appl. No. 11/152,562, Mail Date Mar. 31, 2010, Office Action.
U.S. Appl. No. 11/198,811, Mail Date Jun. 29, 2010, Notice of Allowance.
U.S. Appl. No. 11/316,775, Mail Date Apr. 16, 2008, Office Action.
U.S. Appl. No. 11/316,775, Mail Date Aug. 6, 2008, Office Action.
U.S. Appl. No. 11/344,891, Mail Date May 7, 2010, Office Action.
U.S. Appl. No. 11/390,586, Mail Date Jul. 6, 2010, Office Action.
U.S. Appl. No. 11/396,141, Mail Date May 4, 2010, Office Action.
U.S. Appl. No. 11/396,731, Mail Date Jun. 29, 2010, Office Action.
U.S. Appl. No. 11/406,203, Mail Date Jun. 18, 2010, Notice of Allowance.
U.S. Appl. No. 11/455,993, Mail Date Feb. 17, 2009, Office Action.
U.S. Appl. No. 11/455,993, Mail Date Dec. 16, 2009, Office Action.
U.S. Appl. No. 11/508,656, Mail Date Dec. 9, 2009, Office Action.
U.S. Appl. No. 11/508,656, Mail Date Mar. 25, 2010, Office Action.
U.S. Appl. No. 11/508,662, Mail Date Dec. 28, 2009, Office Action.
U.S. Appl. No. 11/508,662, Mail Date Apr. 14, 2010, Office Action.
U.S. Appl. No. 11/508,715, Mail Date Jan. 6, 2010, Office Action.
U.S. Appl. No. 11/508,715, Mail Date Apr. 26, 2010, Office Action.
U.S. Appl. No. 11/532,325, Mail Date Jan. 5, 2010, Office Action.
U.S. Appl. No. 11/532,576, Mail Date Mar. 1, 2010, Office Action.
U.S. Appl. No. 11/532,576, Mail Date Apr. 23, 2010, Office Action.
U.S. Appl. No. 11/674,930, Mail Date Jan. 8, 2009, Office Action.
U.S. Appl. No. 11/674,930, Mail Date Jun. 4, 2009, Office Action.
U.S. Appl. No. 11/674,930, Mail Date Jan. 8, 2010, Office Action.
U.S. Appl. No. 11/675,462, Mail Date Dec. 10, 2009, Office Action.
U.S. Appl. No. 11/767,818, Mail Date Dec. 24, 2009, Office Action.
U.S. Appl. No. 11/767,818, Mail Date Mar. 22, 2010, Office Action.
U.S. Appl. No. 11/852,190, Mail Date Jun. 24, 2010, Office Action.
U.S. Appl. No. 11/958,295, Mail Date May 25, 2010, Office Action.

(56) References Cited

OTHER PUBLICATIONS

U.S. Appl. No. 11/959,334, Mail Date Aug. 19, 2009, Office Action.
U.S. Appl. No. 11/959,334, Mail Date Jan. 12, 2010, Notice of Allowance.
U.S. Appl. No. 11/959,334, Mail Date Apr. 14, 2010, Notice of Allowance.
U.S. Appl. No. 12/106,928, Mail Date May 10, 2010 Office Action.
U.S. Appl. No. 12/113,851, Mail Date Apr. 27, 2010, Office Action.
U.S. Appl. No. 12/113,851, Mail Date Jun. 24, 2010, Office Action.
U.S. Appl. No. 12/402,398, Mail Date Mar. 9, 2010, Office Action.
U.S. Appl. No. 12/402,398, Mail Date May 20, 2010, Office Action.
U.S. Appl. No. 12/403,256, Mail Date Mar. 30, 2010, Office Action.
U.S. Appl. No. 29/296,370, Mail Date Feb. 10, 2010, Issue Notification.
U.S. Appl. No. 12/135,858, Mail Date Jul. 13, 2011, Office Action.
U.S. Appl. No. 10/786,444, Mail Date Jul. 11, 2013, Notice of Allowance.
U.S. Appl. No. 11/532,325, Mail Date Jul. 17, 2013, Office Action.
U.S. Appl. No. 13/030,922, Mail Date Jul. 18, 2013, Office Action.
U.S. Appl. No. 13/525,839, Mail Date Jul. 15, 2013, Notice of Allowance.
U.S. Appl. No. 13/615,547, Mail Date Jul. 10, 2013, Issue Notification.
U.S. Appl. No. 10/435,104, Mail Date Jul. 23, 2009, Notice of Allowance.
U.S. Appl. No. 10/669,313, Mail Date Oct. 31, 2005, Office Action.
U.S. Appl. No. 11/113,549, Mail Date Jul. 6, 2010, Office Action.
U.S. Appl. No. 11/959,334, Mail Date Jul. 23, 2010, Notice of Allowance.
U.S. Appl. No. 12/403,277, Mail Date Jul. 8, 2010, Office Action.
U.S. Appl. No. 12/955,859, Mail Date Jul. 21, 2011, Office Action.
U.S. Appl. No. 10/682,459, Mail Date Aug. 10, 2011, Issue Notification.
U.S. Appl. No. 11/675,462, Mail Date Aug. 16, 2012, Issue Notification.
U.S. Appl. No. 11/744,089, Mail Date Aug. 8, 2012, Office Action.
U.S. Appl. No. 12/481,377, Mail Date Aug. 10, 2012, Notice of Allowance.
U.S. Appl. No. 12/850,242, Mail Date Aug. 6, 2012, Office Action.
U.S. Appl. No. 12/955,859, Mail Date Aug. 6, 2012, Office Action.
U.S. Appl. No. 11/396,141, Mail Date Aug. 21, 2013, Office Action.
U.S. Appl. No. 13/028,041, Mail Date Aug. 21, 2013, Notice of Allowance.
U.S. Appl. No. 13/490,143, Mail Date Aug. 21, 2013, Issue Notification.
U.S. Appl. No. 12/608,769, Mail Date Aug. 22, 2012, Office Action.
U.S. Appl. No. 12/642,319, Mail Date Aug. 28, 2012, Office Action.
U.S. Appl. No. 12/684,562, Mail Date Aug. 21, 2012, Office Action.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 10/006,400, Mail Date Aug. 2, 2010, Notice of Allowance.
U.S. Appl. No. 10/517,004, Mail Date Aug. 3, 2010, Notice of Allowance.
U.S. Appl. No. 10/541,083, Mail Date Aug. 17, 2010, Notice of Allowance.
U.S. Appl. No. 11/048,503, Mail Date Jul. 30, 2010, Notice of Allowance.
U.S. Appl. No. 11/427,309, Mail Date May 28, 2008, Office Action.
U.S. Appl. No. 11/427,309, Mail Date Jan. 2, 2009, Office Action.
U.S. Appl. No. 11/427,309, Mail Date Apr. 20, 2009, Office Action.
U.S. Appl. No. 11/427,309, Mail Date Nov. 6, 2009, Office Action.
U.S. Appl. No. 11/427,309, Mail Date Apr. 26, 2010, Office Action.
U.S. Appl. No. 11/757,108, Mail Date Nov. 25, 2009, Office Action.
U.S. Appl. No. 13/222,899, filed Aug. 31, 2011, Carley et al.
U.S. Appl. No. 12/143,020, Mail Date Aug. 31, 2011, Office Action.
U.S. Appl. No. 12/897,358, Mail Date Aug. 22, 2011, Office Action.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 13/026,989, Mail Date Aug. 23, 2013, Office Action.
U.S. Appl. No. 13/308,227, Mail Date Sep. 11, 2013, Office Action.
U.S. Appl. No. 09/866,551, filed May 25, 2001, Ginn.
U.S. Appl. No. 10/638,115, Mail Date Aug. 13, 2010, Notice of Allowance.
U.S. Appl. No. 10/787,073, Mail Date Aug. 25, 2010, Notice of Allowance.
U.S. Appl. No. 11/508,656, Mail Date Aug. 30, 2010, Office Action.
U.S. Appl. No. 11/675,462, Mail Date Aug. 13, 2010, Office Action.
U.S. Appl. No. 11/958,281, Mail Date Sep. 2, 2010, Office Action.
U.S. Appl. No. 12/403,256, Mail Date Aug. 19, 2010, Notice of Allowance.
U.S. Appl. No. 13/026,989, Mail Date Sep. 16, 2011, Office Action.
U.S. Appl. No. 12/122,603, Mail Date Sep. 23, 2010, Office Action.
U.S. Appl. No. 12/393,877, Mail Date Sep. 29, 2011, Office Action.
U.S. Appl. No. 12/402,398, Mail Date Sep. 20, 2012, Office Action.
U.S. Appl. No. 12/688,065, Mail Date Oct. 12, 2012, Office Action.
U.S. Appl. No. 12/846,642, Mail Date Sep. 20, 2012, Office Action.
U.S. Appl. No. 12/987,792, Mail Date Sep. 17, 2012, Office Action.
U.S. Appl. No. 10/616,832, Mail Date Sep. 20, 2010, Notice of Allowance.
U.S. Appl. No. 10/787,073, Mail Date Sep. 15, 2010, Issue Notification.
U.S. Appl. No. 11/152,562, Mail Date Sep. 16, 2010, Notice of Allowance.
U.S. Appl. No. 11/427,297, Mail Date Sep. 15, 2010, Office Action.
U.S. Appl. No. 11/767,818, Mail Date Sep. 30, 2010, Office Action.
U.S. Appl. No. 12/365,397, Mail Date Sep. 13, 2010, Office Action.
U.S. Appl. No. 10/356,214, Mail Date Sep. 3, 2010, Notice of Allowance.
U.S. Appl. No. 10/435,104, Mail Date Oct. 5, 2010, Notice of Allowance.
U.S. Appl. No. 10/682,459, Mail Date Oct. 12, 2010, Office Action.
U.S. Appl. No. 11/406,203, Mail Date Oct. 6, 2010, Issue Notification.
U.S. Appl. No. 11/532,576, Mail Date Oct. 13, 2010, Notice of Allowance.
U.S. Appl. No. 11/958,281, Mail Date Oct. 8, 2010, Office Action.
U.S. Appl. No. 12/114,031, Mail Date Oct. 5, 2010, Office Action.
U.S. Appl. No. 12/403,277, Mail Date Oct. 12, 2010, Office Action.
U.S. Appl. No. 11/508,715, Mail Date Oct. 18, 2010, Office Action.
U.S. Appl. No. 10/667,144, Mail Date Oct. 28, 2011, Notice of Allowance.
U.S. Appl. No. 12/945,646, Mail Date Oct. 26, 2011, Office Action.
U.S. Appl. No. 10/264,306, Mail Date Oct. 29, 2010, Notice of Allowance.
U.S. Appl. No. 12/106,928, Mail Date Oct. 25, 2010, Office Action.
U.S. Appl. No. 11/427,297, Mail Date Oct. 31, 2012, Issue Notification.
U.S. Appl. No. 12/114,091, Mail Date Nov. 8, 2012, Office Action.
U.S. Appl. No. 12/403,277, Mail Date Nov. 5, 2012, Office Action.
U.S. Appl. No. 12/608,769, Mail Date Nov. 5, 2012, Notice of Allowance.
U.S. Appl. No. 12/684,400, Mail Date Oct. 16, 2012, Office Action.
U.S. Appl. No. 12/848,642, Mail Date Nov. 9, 2012, Office Action.
U.S. Appl. No. 12/850,242, Mail Date Oct. 17, 2012, Office Action.
U.S. Appl. No. 13/039,087, Mail Date Nov. 6, 2012, Notice of Allowance.
U.S. Appl. No. 10/517,004, Mail Date Nov. 23, 2010, Issue Notification.
U.S. Appl. No. 12/114,031, Mail Date Nov. 22, 2010, Office Action.
U.S. Appl. No. 12/403,256, Mail Date Nov. 23, 2010, Issue Notification.
U.S. Appl. No. 12/961,331, filed Dec. 6, 2010, Voss.
U.S. Appl. No. 10/147,774, Mail Date Dec. 2, 2010, Notice of Allowance.

(56) References Cited

OTHER PUBLICATIONS

U.S. Appl. No. 10/541,083, Mail Date Dec. 1, 2010, Issue Notification.
U.S. Appl. No. 11/959,334, Mail Date Nov. 10, 2010, Issue Notification.
U.S. Appl. No. 12/393,877, Mail Date Dec. 13, 2011, Office Action.
U.S. Appl. No. 12/941,809, Mail Date Dec. 13, 2011, Restriction Requirement.
U.S. Appl. No. 12/338,977, Mail Date Nov. 28, 2012, Office Action.
U.S. Appl. No. 12/961,331, Mail Date Dec. 4, 2012, Office Action.
U.S. Appl. No. 13/030,922, Mail Date Dec. 18, 2012, Office Action.
U.S. Appl. No. 12/897,358, filed Oct. 4, 2010, Carley.
U.S. Appl. No. 12/966,923, filed Dec. 13, 2010, Cummins et al.
U.S. Appl. No. 11/048,503, Mail Date Dec. 8, 2012, Issue Notification.
U.S. Appl. No. 12/113,851, Mail Date Dec. 16, 2010, Office Action.
U.S. Appl. No. 12/114,091, Mail Date Dec. 17, 2010, Office Action.
U.S. Appl. No. 12/684,470, Mail Date Dec. 20, 2011, Restriction Requirement.
U.S. Appl. No. 12/684,569, Mail Date Dec. 20, 2011, Restriction Requirement.
U.S. Appl. No. 11/675,462, Mail Date Dec. 22, 2011, Notice of Allowance.
U.S. Appl. No. 12/143,020, Mail Date Feb. 23, 2012, Notice of Allowance.
U.S. Appl. No. 12/548,274, Mail Date Mar. 2, 2012, Office Action.
U.S. Appl. No. 12/642,319, Mail Date Feb. 27, 2012, Office Action.
U.S. Appl. No. 13/308,227, filed Nov. 30, 2011, Yibarren.
U.S. Appl. No. 12/688,065, Mail Date Apr. 26, 2012, Office Action.
U.S. Appl. No. 13/525,839, filed Jun. 18, 2012, Carley et al.
U.S. Appl. No. 11/427,297, Mail Date Jun. 26, 2012, Notice of Allowance.
U.S. Appl. No. 11/767,818, Mail Date Jul. 4, 2012, Issue Notification.
U.S. Appl. No. 12/338,977, Mail Date Jul. 11, 2012, Office Action.
U.S. Appl. No. 11/396,731, Mail Date Sep. 1, 2011, Office Action.
U.S. Appl. No. 12/548,274, Mail Date Sep. 10, 2012, Office Action.
U.S. Appl. No. 12/684,470, Mail Date Aug. 30, 2012, Office Action.
U.S. Appl. No. 12/684,542, Mail Date Sep. 13, 2012, Office Action.
U.S. Appl. No. 11/427,309, Mail Date Nov. 15, 2010, Office Action.
U.S. Appl. No. 10/147,774, Mail Date Apr. 6, 2011, Issue Notification.
U.S. Appl. No. 13/028,041, filed Feb. 15, 2011, Von Oepen.
U.S. Appl. No. 13/112,618, filed May 20, 2011, Gianotti et al.
U.S. Appl. No. 13/112,631, filed May 20, 2011, Voss.
U.S. Appl. No. 12/955,859, Mail Date May 26, 2011, Office Action.
U.S. Appl. No. 11/390,586, Mail Date Jul. 18, 2012, Issue Notification.
U.S. Appl. No. 12/608,773, Mail Date Jul. 20, 2012, Office Action.
U.S. Appl. No. 12/684,569, Mail Date Jul. 30, 2012, Office Action.
U.S. Appl. No. 13/039,087, Mail Date Jul. 17, 2012, Office Action.
U.S. Appl. No. 10/908,721, Mail Date Jul. 18, 2013, Notice of Allowance.
U.S. Appl. No. 11/744,089, Mail Date Aug. 8, 2013, Notice of Allowance.
U.S. Appl. No. 12/850,242, Mail Date Aug. 6, 2013, Notice of Allowance.
U.S. Appl. No. 12/955,859, Mail Date Aug. 1, 2013, Notice of Allowance.
U.S. Appl. No. 13/615,547, Mail Date Aug. 7, 2013, Issue Notification.
U.S. Appl. No. 11/675,462, Mail Date Aug. 3, 2011, Office Action.
U.S. Appl. No. 12/114,031, Mail Date Aug. 2, 2011, Office Action.
U.S. Appl. No. 12/955,859, Mail Date Dec. 15, 2011, Office Action.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 13/017,636, filed Jan. 31, 2011, Carley et al.
U.S. Appl. No. 13/026,989, filed Feb. 14, 2011, Cummins.
U.S. Appl. No. 10/264,306, Mail Date Feb. 16, 2011, Issue Notfication.
U.S. Appl. No. 11/767,818, Mail Date Feb. 16, 2011, Office Action.
U.S. Appl. No. 10/638,115, Mail Date Dec. 22, 2010, Issue Notification.
U.S. Appl. No. 12/402,398, Mail Date Mar. 13, 2013, Notice of Allowance.
U.S. Appl. No. 13/028,041, Mail Date Jan. 4, 2013, Office Action.
U.S. Appl. No. 13/028,041, Mail Date Feb. 26, 2013, Office Action.
Turn—macmillandictionary.com/dictionary.american/turn.
Turn—Merriam-webster.com/dictionary/turn.
U.S. Appl. No. 11/396,141, Mail Date Nov. 4, 2013, Notice of Allowance.
U.S. Appl. No. 11/532,325, Mail Date Dec. 2, 2013, Office Action.
U.S. Appl. No. 11/852,190, Mail Date Nov. 26, 2013, Office Action.
U.S. Appl. No. 12/106,928, Mail Date Dec. 2, 2013, Office Action.
U.S. Appl. No. 12/122,603, Mail Date Nov. 20, 2013, Office Action.
U.S. Appl. No. 12/642,319, Mail Date Dec. 16, 2013, Office Action.
U.S. Appl. No. 12/688,065, Mail Date Oct. 18, 2013, Office Action.
U.S. Appl. No. 12/941,809, Mail Date Nov. 8, 2013, Office Action.
U.S. Appl. No. 12/961,331, Mail Date Sep. 20, 2013, Advisory Action.
U.S. Appl. No. 13/052,634, Mail Date Nov. 8, 2013, Office Action.
U.S. Appl. No. 13/112,618, Mail Date Nov. 20, 2013, Office Action.
U.S. Appl. No. 13/112,631, Mail Date Dec. 2, 2013, Office Action.
U.S. Appl. No. 13/153,594, Mail Date Oct. 16, 2013, Notice of Allowance.
U.S. Appl. No. 13/308,227, Mail Date Dec. 2, 2013, Interview Summary.
U.S. Appl. No. 13/791,829, Mail Date Oct. 8, 2013, Notice of Allowance.
U.S. Appl. No. 11/198,811, Mail Date Oct. 20, 2010, Issue Notification.
U.S. Appl. No. 11/508,662, Mail Date Oct. 26, 2010, Office Action.
U.S. Appl. No. 11/852,190, Mail Date Nov. 1, 2010, Office Action.
U.S. Appl. No. 12/114,091, Mail Date Oct. 27, 2010, Office Action.
U.S. Appl. No. 12/106,928, filed Apr. 21, 2008, Ginn et al.
U.S. Appl. No. 12/106,937, filed Apr. 21, 2008 Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 11/427,309, Mail Date Jun. 7, 2013, Notice of Allowance.
U.S. Appl. No. 13/112,618, Mail Date Jun. 7, 2013, Office Action.
U.S. Appl. No. 13/488,233, Mail Date Jun. 5, 2013, Issue Notification.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, Mail Date Jan. 13, 2010, Notice of Allowance.
U.S. Appl. No. 11/113,549, Mar. 14, 2014, Notice of Allowance.
U.S. Appl. No. 11/396,141, Mar. 19, 2014, Issue Notification.
U.S. Appl. No. 11/852,190, Feb. 12, 2014, Notice of Allowance.
U.S. Appl. No. 12/106,937, Jan. 22, 2014, Office Action.
U.S. Appl. No. 12/848,642, Feb. 3, 2014, Notice of Allowance.
U.S. Appl. No. 12/941,809, Feb. 3, 2014, Notice of Allowance.
U.S. Appl. No. 12/987,792, Jan. 21, 2014, Office Action.
U.S. Appl. No. 13/030,922, Jan. 8, 2014, Notice of Allowance.
U.S. Appl. No. 13/222,899, Jan. 10, 2014, Office Action.
U.S. Appl. No. 13/898,202, Jan. 3, 2014, Office Action.

* cited by examiner

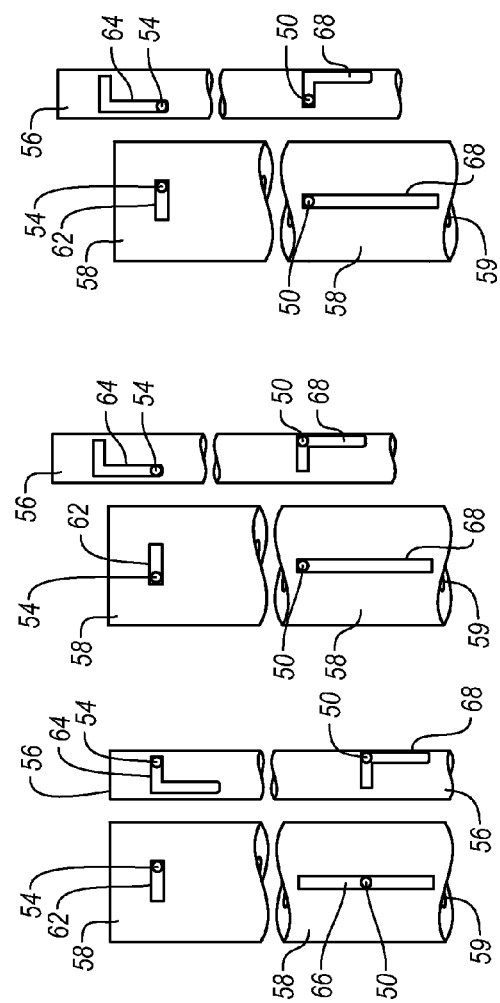

VASCULAR SHEATH WITH BIOABSORBABLE PUNCTURE SITE CLOSURE APPARATUS AND METHODS OF USE

REFERENCE TO RELATED APPLICATIONS

This application is a continuation of U.S. patent application Ser. No. 10/264,306, filed Oct. 3, 2002, now U.S. Pat. No. 7,901,428, which is a continuation of U.S. patent application Ser. No. 09/546,998, filed Apr. 11, 2000, now U.S. Pat. No. 6,461,364, which is a continuation-in-part of U.S. patent application Ser. No. 09/478,179 filed Jan. 5, 2000, now U.S. Pat. No. 6,197,042, the disclosures of which are incorporated by reference herein.

FIELD OF THE INVENTION

The present invention relates to apparatus and methods for sealing an iatrogenic puncture in a vessel formed in conjunction with a diagnostic or therapeutic treatment. More particularly, the present invention provides apparatus comprising an introducer sheath including a puncture site closure device comprising a bioabsorbable clip.

BACKGROUND OF THE INVENTION

Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurses's time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al. describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art, Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, such devices employing resilient or deformable clips have been developed. U.S. Pat. No. 5,478,354 to Tovey et al. describes the use of resilient clips in conjunction with a trocar to close abdominal puncture wounds. U.S. Pat. No. 5,810,846 to Virnich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft having a distal end formed with one or more opposed pairs of resilient grasping prongs and that is advanced over a guide wire through a coaxial hollow tube to a position at the distal end of the tube just proximal of the puncture. The grasping prongs are extended beyond the distal end of the tube to grasp the vessel on opposing sides of the puncture. The shaft then is partially retracted, causing the prongs to contract within the tube, thereby sealing the puncture site.

The percutaneous puncture closure devices described in the foregoing patents have the drawback that a separate device must be deployed through the introducer sheath to close the puncture site, thus prolonging the procedure. Moreover, these devices generally require relatively complex apparatus and involve time consuming manipulation to achieve hemostasis.

In view of the foregoing, it would be desirable to provide apparatus and methods suitable for vascular puncture closure that overcome the disadvantages of previously known devices.

It also would be desirable to provide apparatus and methods that quickly and effectively achieve hemostasis.

It further would be desirable to provide vascular puncture closure apparatus and methods that do not require the introduction of additional apparatus at the completion of the catheterization procedure to achieve closure.

It still further would be desirable to provide apparatus and methods wherein all foreign materials left in a patient's body are bioabsorbable.

It would be desirable to provide vascular puncture closure apparatus and methods that are safe, lower cost, and easy to use.

SUMMARY OF THE INVENTION

In view of the foregoing, it is an object of the present invention to provide vascular puncture closure apparatus and methods that overcome disadvantages of previously known devices.

It also is an object of this invention to provide apparatus and methods suitable for vascular puncture closure that quickly and effectively achieve hemostas is.

It is a further object of the present invention to provide apparatus and methods for vascular puncture closure that do not require the introduction of additional apparatus at the completion of the catheterization procedure to achieve closure.

It is still further an object of the present invention to provide apparatus and methods wherein all foreign materials left in a patient's body are bioabsorbable.

It is yet another object of the present invention to provide vascular puncture closure apparatus and methods that are safe, lower cost, and easy to use.

These and other objects of the present invention are accomplished by providing a vascular introducer sheath having an integrated wound closure component. The closure component consists of a bioabsorbable and deformable clip with a bioabsorbable fastener and is disposed on and advanceable over the exterior of the introducer sheath in an expanded delivery configuration until opposite sides of the clip pierce a vessel on opposite sides of a puncture site. The clip is then mechanically deformed with the fastener into a deployed configuration, thereby drawing opposite sides of the puncture together and closing the wound. Means also are provided for confirming when the bioabsorbable clip has engaged the vessel wall to indicate to the surgeon that the clip may be deployed and the introducer sheath may be withdrawn.

In a preferred embodiment, the bioabsorbable clip resembles an inverted "Y" with pointed ends that puncture the vessel to be closed. The fastener comprises a bioabsorbable locking collar that may be advanced down the length of the clip to bring the pointed ends together.

In a second embodiment, the bioabsorbable clip comprises a hoop with pointed legs extending therefrom. The hoop has two points of reduced thickness spaced 180 degrees apart on the circumference of the hoop. The fastener comprises a bioabsorbable conical wedge that is pushed down into the hoop to force opposing sides of the hoop towards one another and bring the pointed legs together.

Advantageously, the wound closure component of the present invention is inexpensively integrated into a standard-size introducer sheath, thereby eliminating the need for a separate closure device at the conclusion of a catheterization procedure. The present invention provides quick, safe, effective, and easy-to-use apparatus for achieving vascular closure that overcome drawbacks of previously known devices. Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 5A-5B through 8A-8B are side-sectional views of the closure component of FIG. 2A in use at a vascular puncture site, with corresponding side views of the proximal and distal slots of FIGS. 2B and 2C, illustrating a method of sealing the puncture site with the present invention.

DETAILED DESCRIPTION OF THE INVENTION

The integrated vascular introducer sheath with closure component of the present invention overcomes disadvantages associated with previously known methods and apparatus for sealing a vascular puncture by providing a quick, simple, safe, lower cost, effective, and easy-to-use solution to wound closure. Apparatus constructed in accordance with the present invention provide vascular introduction and wound closure in a single device, eliminating the time and manipulation required to insert a separate closure device at the completion of a procedure.

Figure 1:
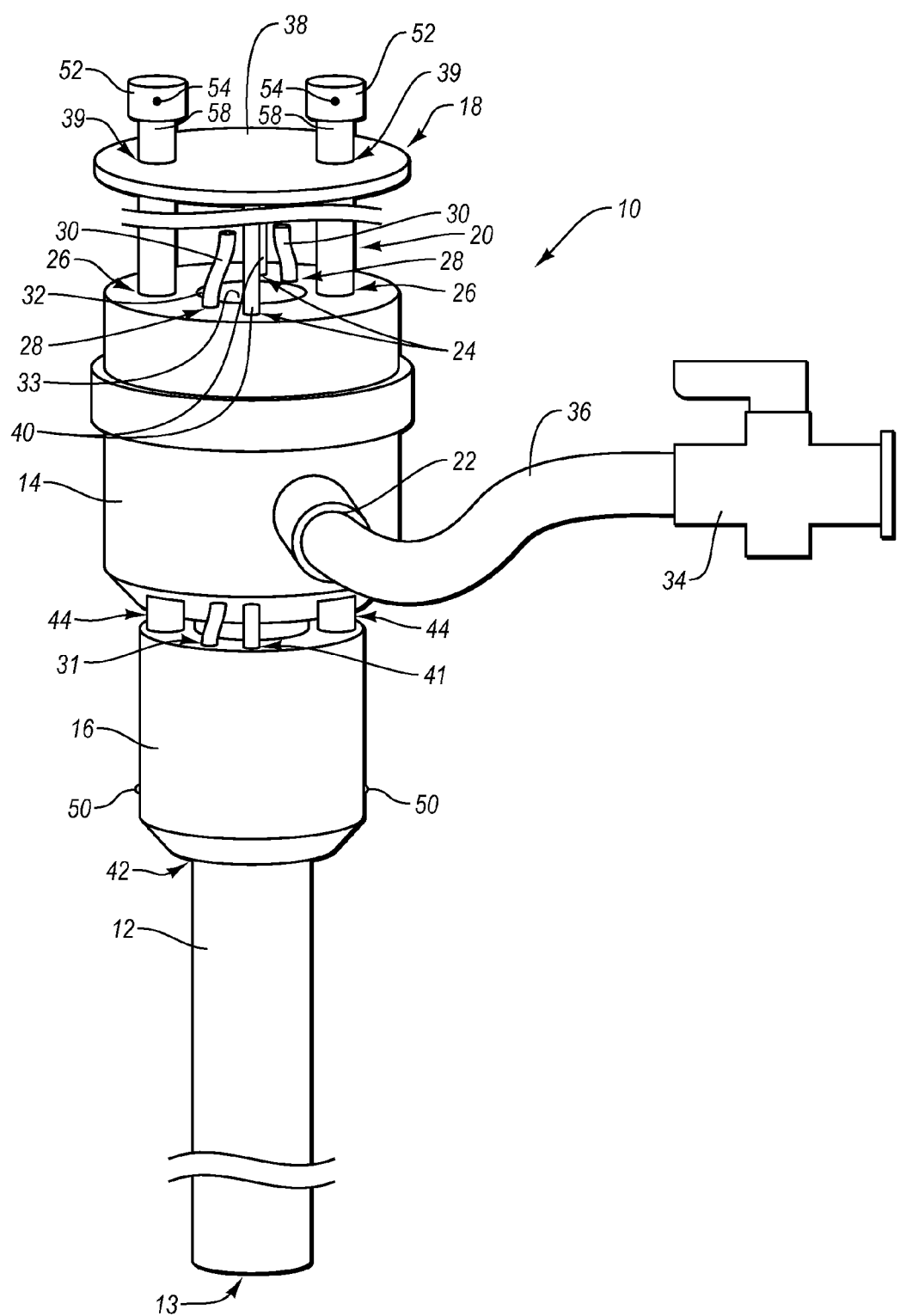
FIG. 1 is a side view of an integrated vascular device constructed in accordance with the present invention.

Referring to FIG. 1, a first embodiment of apparatus of the present invention is described. Vascular device 10 comprises introducer sheath 12 coupled to hub 14, clip housing 16 and clip actuator 18. A closure component 20, as described in detail hereinbelow, is disposed in clip housing 16.

Introducer sheath 12 comprises a material typically used for vascular introducer sheaths, such as polyethylene or nylon, and includes central lumen 13 through which other interventional devices may be introduced into the vasculature, for example, to perform a diagnostic or interventional procedure such as angiography, angioplasty, or stenting.

Hub 14 is mounted to the proximal end of introducer sheath 12 and includes side port 22, actuator lumens 24, closure lumens 26, backbleed lumens 28, backbleed tubes 30, and device port 32. Device port 32 communicates with central lumen 13 of introducer sheath 12, and has self-sealing elastomeric membrane 33 disposed across it. Self-sealing membrane 33, which may comprise, e.g., latex or a biocompatible synthetic rubber, permits interventional devices to be introduced through device port 32, while preventing blood loss through central lumen 13. Side port 22 of hub 14 is also in communication with central lumen 13, and is connected to hemostatic port 34 via biocompatible tubing 36.

Clip housing 16 includes two lumens, as described hereinbelow, that each hold a bioabsorbable, deformable clip. In accordance with the principles of the present invention, clip housing 16 is slidably disposed on the exterior of introducer sheath 12 and is movable from a stowed position, adjacent hub 14, to a distal clip deployment position, where the bioabsorbable clip is urged into engagement with tissue surrounding a vascular puncture. Clip housing 16 prevents the clips from snagging on tissue during advancement of clip housing 16.

Clip actuator 18 comprises plunger 38 and rods 40, which are configured to slidably pass through actuator lumens 24 of hub 14. Plunger 38 further includes openings 39. The distal ends of rods 40 are mounted in clip housing 16, so that movement of plunger 38 causes corresponding proximal or distal movement of clip housing 16. As described in detail hereinafter, when plunger 38 is moved to its proximal-most position, clip housing 16 is disposed adjacent to hub 14 and provides adequate clearance for interventional devices to be inserted through device port 32 and central lumen 13 into the patient's vasculature. When moved to its distal-most position, plunger 38 causes rods 40 to urge clip housing 16 distally.

Figures 2A, 2B, 2C:
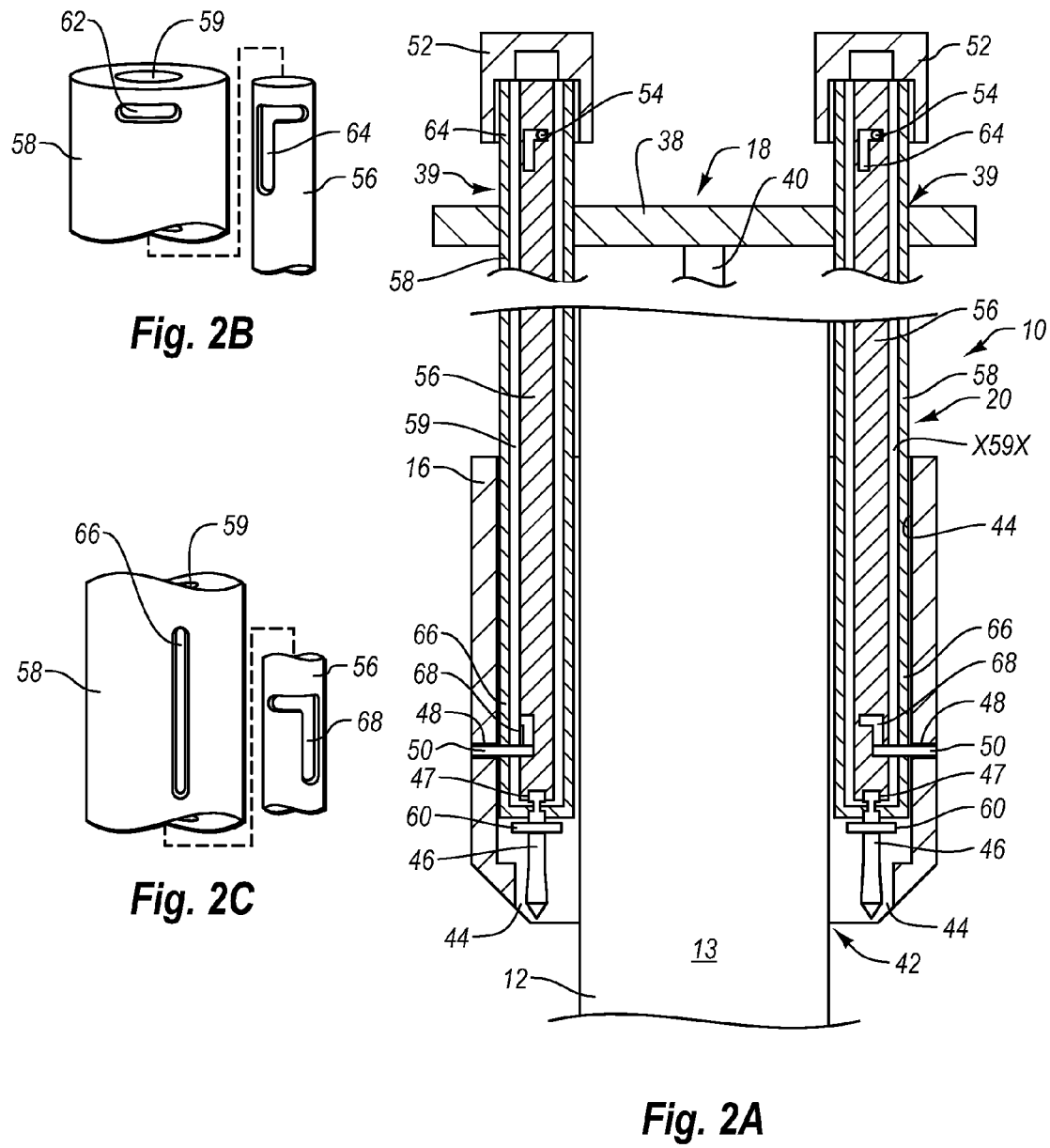
FIGS. 2A-2C are, respectively, a cross-sectional view of a closure component of the vascular device of FIG. 1, an exploded side view of proximal slots of the closure component, and an exploded side view of distal slots.

Referring now also to FIG. 2, closure component 20 of vascular device 10 is described in greater detail. Clip housing 16 comprises lumen 42 that slidably receives introducer sheath 12, rod bores 41 (see FIG. 1) in which rods 40 are mounted, clip lumens 44 in which bioabsorbable clips 46 are housed and advanced to a puncture site, pin holes 48 for rigidly receiving distal pins 50, and backbleed indicator ports (not shown, out of the plane of the cross-section of FIG. 2A) that are coupled to backbleed tubes 30 via blood lumens 31.

Closure component 20 further comprises caps 52 with pin holes (not shown, out of the plane of the cross-section of FIG. 2A) configured to receive proximal pins 54, clip holders 56 attached to bioabsorbable clips 46, and locking collar drivers 58 configured to advance fasteners 60. Locking collar drivers 58 are slidably received within lumens 39 of plunger 38, closure lumens 26 of hub 14, and clip lumens 44 of clip housing 16. Drivers 58 further comprise lumens 59 and square clip bores 47, in which clip holders 56 and clips 46, respectively, are slidably received. Bores 47 are of square cross section.

As illustrated in FIG. 2B, locking collar drivers 58 comprise proximal driver slots 62 that communicate with lumens 59, while clip holders 56 comprise proximal holder slots 64. Proximal pins 54, mounted in caps 52, pass through and are slidably received within slots 62 and 64. As seen in FIG. 2C, locking collar drivers 58 further comprise distal driver slots 66 that communicate with lumens 59, while clip holders 56 further comprise distal holder slots 68. Distal pins 50, mounted in clip housing 16, pass through and are slidably received within slots 66 and 68.

As discussed hereinabove, backbleed indicator ports (not shown) are coupled to backbleed tubes 30 via blood lumens 31 that extend through clip housing 16. Backbleed tubes 30 are slidably disposed through backbleed lumens 28 of hub 14. When the distal end of clip housing 16 is advanced distally against a vessel wall at a vascular puncture, blood enters the backbleed indicator ports and exits through tubes 30, providing visual confirmation to an operator that the distal end of clip housing 16 is positioned adjacent to the vessel wall. Backbleed tubes 30 thus enable the operator to determine when clip housing 16 has been sufficiently advanced to permit clip deployment, while reducing the risk that the clip is either deployed short of the puncture site or extended into the vessel.

In conjunction with clip deployment, a bioglue or tissue sealant may be delivered through hemostatic port 34, biocompatible tubing 36, side port 22 and central lumen 13 of introducer sheath 12 to the vascular puncture to further help seal the vessel after deployment of clips 46. Alternatively, the bioglue or tissue sealant may be delivered through device port 32 or through the backbleed path described above.

Figure 3A:
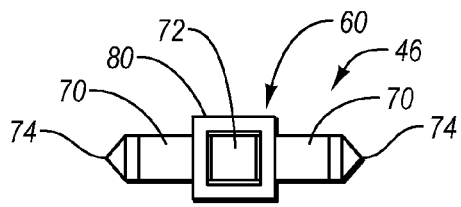
FIGS. 3A-3C are, respectively, views of a bioabsorbable clip and fastener of the present invention shown in top view in a delivery configuration, in side view in the delivery configuration, and in side view in a deployed configuration.
Figure 3C:
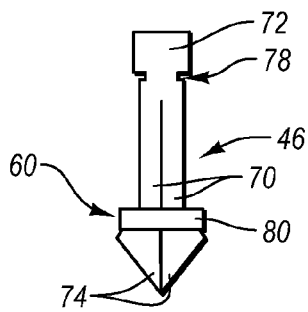
Figure 3B:
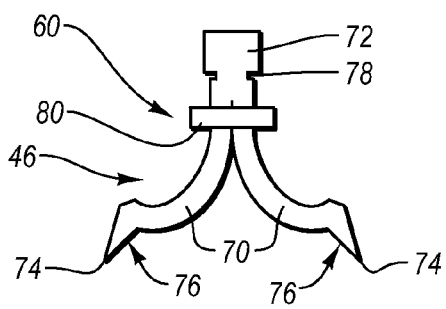

With reference now to FIGS. 3A-3C, bioabsorbable clip 46 and fastener 60 are described in greater detail. FIG. 3A shows clip 46 in the delivery configuration. Clip 46 comprises curved legs 70 and proximal end 72. Legs 70 distally terminate at spikes 74 with optional engagement means 76, and proximally terminate at narrowed region 78. Engagement means 76 may comprise, for example, barbs or hooks. As seen in FIG. 2A, proximal end 72 attaches to clip holder 56 by, for example, adhesive, and is slidably received by square clip bore 47 of locking collar driver 58. As with bore 47, clip 46 is of substantially square cross section.

Fastener 60 comprises bioabsorbable locking collar 80, which is slidably received on the exterior of clip 46. As seen in FIG. 3B, locking collar 80 may be distally advanced down the exterior of clip 46 to deform the clip to its deployed configuration, wherein curved legs 70 and spikes 74 are drawn together. Clip 46 may then be separated from clip holder 56 by rotating proximal end 72 with respect to legs 70, causing the clip to snap into two pieces at narrowed region 78, for the reasons described hereinafter. Clip 46 and locking collar 80 preferably are fabricated from bioabsorbable materials, such as polyglycolic acid.

Figure 4A:
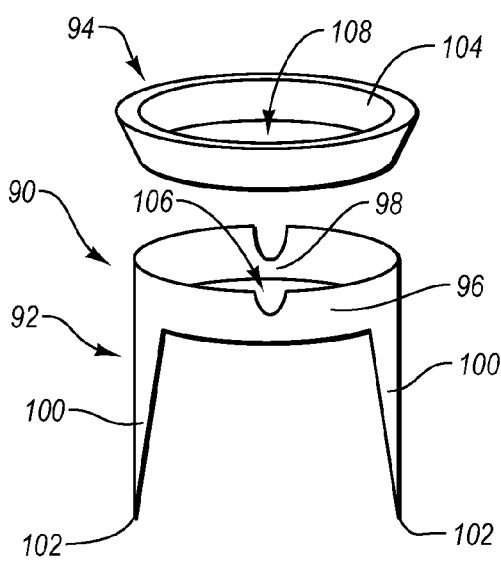
FIGS. 4A and 4B are isometric views of an alternative embodiment of the bioabsorbable surgical clip and fastener, constructed in accordance with the present invention and shown, respectively, in a delivery configuration and in a deployed configuration.
Figure 4B:
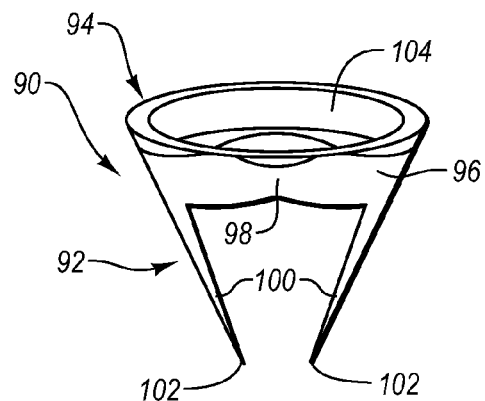

Referring to FIG. 4, an alternative embodiment of the closure component of the present invention is described. Closure component 90 comprises bioabsorbable clip 92 and fastener 94. Clip 92 comprises proximal hoop 96 with narrowed regions 98, and legs 100 terminating in spikes 102. Fastener 94 comprises bioabsorbable wedge 104. Wedge 104 has a diameter substantially equal to the diameter of hoop 96 at its distal end, the diameter tapering to a maximum diameter at the proximal end of wedge 104. Clip 92 therefore may be deformed from the delivery configuration of FIG. 4A to the deployed configuration of FIG. 4B, wherein legs 100 and spikes 102 are drawn together, by advancing wedge 104 into hoop 96 to deform clip 92 at narrowed regions 98. Lumen 106 extends through hoop 98 of clip 92, while lumen 108 extends through wedge 96. Clip 92 and wedge 96 therefore are configured for delivery over the exterior of an introducer sheath. The clip and wedge preferably are fabricated from bioabsorbable materials.

With reference to FIGS. 5A-5B through 8A-8B, in conjunction with FIGS. 1-3, methods of using vascular device 10 are described. Introducer sheath 12 is advanced through skin, fat, and muscle tissue into vessel V, through vascular puncture P, which is formed in accordance with well-known techniques. Vascular device 10 is used in the same manner as a standard introducer sheath, with instruments being advanced into the vessel via lumen 13. Specifically, with plunger 28 and rods 40 in the proximal-most, fully retracted position, an interventional procedure then is performed by introducing one or more interventional devices, e.g. angioplasty balloons, stent delivery systems, atherectomy devices, etc., through device port 32 and lumen 13 of introducer sheath 12 in accordance with well-known techniques. Side port 22 may be used to infuse fluids, e.g., contrast agents or medications, into the vessel through introducer sheath 12 during the interventional procedure.

Upon completion of the procedure, vascular device 10 advantageously may be used to close vascular puncture P. At this point, clip actuator 18, clip housing 16, and closure component 20 with clips 46, are disposed in the proximal-most position adjacent to hub 14.

Clip actuator 18 then is advanced by urging plunger 38 in the distal direction, thus causing rods 40 to slide through actuator lumens 24 of hub 14 and advance clip housing 16. Distal pins 50, mounted in housing 16, abut distal slots 66 and 68 of drivers 58 and holders 56, respectively. Thus, distal advancement of clip housing 16 also distally advances closure component 20. Continued distal advancement of plunger 38 causes the distal end of clip housing 16 to abut against the exterior of the vessel, so that the back bleed indicator ports (not shown) of clip housing 16 directly communicate with the puncture wound. The presence of pressure in the vessel higher than atmospheric pressure causes blood to pass through the indicator ports, through blood lumens 31, and exit through the proximal ends of tubes 30, thus confirming that clip housing 16 is positioned at the puncture site and should not be advanced further.

FIG. 5B illustrates closure component 20 via sectional views through clip housing 16 along planes parallel to introducer sheath 12. FIG. 5A shows the locations of proximal pins 54 within proximal slots 62 and 64, and the locations of distal pins 50 within distal slots 66 and 68, corresponding to the relative longitudinal positions of clip holders 56 and locking collar drivers 58 depicted in FIG. 5B. Pin locations are shown via side views of clip holders 56 and locking collar drivers 58 at the relevant locations.

As seen in FIGS. 5A and 5B, with clip housing 16 positioned at puncture site P, proximal pins 34, mounted in caps 52, are positioned at the extreme right of proximal driver slots 62 and of the circumferential portions of proximal holder slots 64. Distal pins 50 are located at the distal end of distal driver slots 66 and of the longitudinal portions of distal holder slots 68.

In FIGS. 6A and 6B, with clip housing 16 held immobile, force is applied to caps 52 to distally advance clips 46 with respect to housing 16. Specifically, proximal pins 54 abut and apply force against proximal slots 62 and 64, which advances drivers 58 and clip holders 56, as well as attached clips 46 and locking collars 80. Distal pins 50 move freely within distal slots 66 and the longitudinal portions of distal slots 68. Distal advancement of clips 46 continues until pins 50 abut against the proximal end of the longitudinal portions of distal holder slots 68 of clip holders 56. Drivers 58 likewise are restrained by their connection to clip holders 56 via proximal pins 54. The tissue-engaging members, spikes 74 and engagement means 76, of clips 46 contact and pierce the wall of vessel V on opposite sides of the puncture site P.

As seen in FIGS. 7A and 7B, once the spikes have pierced the vessel wall, locking collar drivers 58 are advanced distally while clip housing 16 and clip holders 56 remain stationary, thereby distally advancing locking collars 80 down the exteriors of clips 46 to draw legs 70 and spikes 74 together to close puncture P. Engagement means 76 serve to retain the clips within the vessel wall during healing.

To achieve this advancement of drivers 58 with respect to clip holders 56, caps 52 are rotated clockwise, as viewed from above, until proximal pins 54 abut against the extreme left of proximal slots 62 and 64, thereby aligning the pins with the longitudinal portions of proximal holder slots 64. Then, force is once again applied to caps 52 to advance drivers 58 and deform clips 46 to their deployed configurations. Specifically, proximal pins 54 abut and apply force to proximal driver slots 62, thereby distally advancing drivers 58. Pins 54 move freely within the longitudinal portions of proximal holder slots 64 until they abut against the distal ends of slots 64. Likewise, distal driver slots 66 move freely until distal pins 50 abut the proximal ends of slots 66. In FIG. 7A, when proximal pins 54 abut slots 64 and distal pins 50 abut slots 66, locking collars 80 have been driven down the exteriors of clips 46, thereby deforming the clips to draw legs 70 together and close the puncture site.

In FIGS. 8A and 8B, with clips 46 deformed to seal puncture P, clip holders 56 are detached from clips 46 by snapping the clips free at narrowed regions 78. At this point, or prior to detachment, a suitable biocompatible bioglue or tissue sealant optionally may be injected into the puncture tract, as discussed hereinabove, through device port 32 or side port 22, to aid in sealing vascular puncture P. Alternatively, the bioglue or tissue sealant may be delivered through the backbleed path described above. Vascular device 10 then is withdrawn from the vessel wall, completing the procedure.

Clips 46 are detached from clip holders 56 by rotating caps 52 counterclockwise, as viewed from above. Proximal pins 54 of caps 52 move freely within proximal driver slots 62, but abut against the distal end of the longitudinal portions of proximal holder slots 64 and cause clip holders 56 to rotate with respect to collar drivers 58. Distal pins 50 of clip housing 16 move freely within the circumferential portions of distal holder slots 68 during rotation of clip holders 56. Meanwhile, drivers 58 are restrained from rotation by distal pins 50, which abut against distal driver slots 66. Bioabsorbable clips 46 do not rotate because the square cross section of square clip bores 47 of drivers 58 matches the substantially square cross section of clips 46; thus, since drivers 58 are restrained from rotation, so are clips 46. Non-square cross sections for clips 46 and bores 47, capable of performing the restraining function, will be apparent to those of skill in the art and fall within the scope of the present invention.

Since clips 46 are restrained while clip holders 56 rotate, and since proximal ends 72 of clips 46 are attached to clip holders 56, counterclockwise rotation of caps 52 causes clips 46 to snap at their weakest points: narrowed regions 78. Vascular device 10 may then be removed from the patient to complete the procedure.

Although preferred illustrative embodiments of the present invention are described above, it will be evident to one skilled in the art that various changes and modifications may be made without departing from the invention. For example, with minor modifications, vascular device 10 may be configured to carry closure component 90 of FIG. 4, or any of a variety of alternative bioabsorbable and deformable clips. Proximal pins 54 may be formed integrally with caps 52, and distal pins 50 may be formed integrally with clip housing 16. Any number of clips 46 may be used to close the vascular puncture. It is intended in the appended claims to cover all such changes and modifications that fall within the true spirit and scope of the invention.

What is claimed is:

1. A method for closing an opening in tissue comprising:
providing an apparatus comprising an introducer sheath and an integrated annularly-shaped wound closure mechanism;
advancing said introducer sheath into tissue, through a tissue opening;
providing a housing coupled to and slidably disposed on the exterior of said introducer sheath, said housing cooperating with at least one bleedback tube extending from said housing toward a proximal end of said apparatus;
moving said housing, with said at least one bleedback tube, distally along said introducer sheath to move said wound closure mechanism from a stowed position to a distal deployment position, wherein when said wound closure mechanism is moved from the stowed position to the distal deployment position, the wound closure mechanism being located radially around at least a portion of the introducer sheath.

2. The method of claim 1, further comprising advancing said integrated wound closure mechanism and an integrated wound closure component that comprises at least two elongated tissue-piercing members.

3. The method of claim 2, wherein said tissue-piercing members comprise spikes.

4. The method of claim 2, wherein said integrated wound closure component is provided with spikes which pierce the tissue and wherein when said integrated wound closure mechanism is moved from a stowed position to a distal deployment position, a deforming step comprises urging said spikes toward each other.

5. The method of claim 2, wherein said integrated wound closure component has longitudinally extending legs which comprise at least two elongated tissue-piercing members and wherein when said integrated wound closure mechanism is moved from a stowed position to a distal deployment position opposing legs of the wound closure component are directed inwardly towards one another.

6. The method of claim 1, further comprising before moving said wound closure mechanism from a stowed position to a distal deployment position:
performing an interventional procedure through the introducer sheath.

7. A method for sealing a puncture in tissue comprising:
providing an apparatus comprising an introducer sheath with a proximal hub, a closure mechanism, and an integrated annularly-shaped wound closure component that includes at least two elongated tissue-piercing members;
advancing said introducer sheath into a vessel, through a vascular puncture;
providing a housing slidably disposed on and exterior to said introducer sheath, said housing cooperating with at least one bleedback tube extending from said housing toward said hub and being slidably received within said hub;
moving said housing, with said at least one bleedback tube, distally along said introducer sheath to move said wound closure component from a stowed position toward a distal deployment position, wherein when said wound closure component is moved from the stowed position to the distal deployment position, said wound closure component being located radially around at least a portion of said introducer sheath
directing tissue near the puncture in said vessel together to limit liquid flowing through the puncture following healing of the puncture.

8. The method of claim 7, wherein said integrated wound closure component comprises at least two elongated tissue-piercing members.

9. The method of claim 8, wherein said tissue-piercing members comprise spikes.

10. The method of claim 7, wherein said integrated wound closure component is provided with spikes which pierce the vessel wall and wherein when said integrated wound closure component is moved from a stowed position to a distal deployment position, a deforming step comprises urging said spikes toward each other.

11. The method of claim 7, wherein said integrated wound closure component has longitudinally extending legs which comprise at least two elongated tissue-piercing members and wherein when said integrated wound closure component is moved from a stowed position to a distal deployment position opposing legs of the wound closure component are directed inwardly towards one another.

12. The method of claim 7, further comprising before moving said wound closure component from a stowed position to a distal deployment position:
performing an interventional procedure through the introducer sheath.

13. A method for vascular puncture closure comprising:
providing an apparatus comprising a housing having at least one lumen and an integrated annularly-shaped wound closure mechanism cooperating with said at least one lumen, said housing comprising a bleedback lumen coupled with a bleedback tube extending proximally from said housing towards a proximal end of said apparatus, said bleedback tube being movable with said housing;
advancing said housing, with said bleedback tube, distally along said apparatus to advance said lumen into a vessel through a vascular puncture, wherein when said integrated wound closure mechanism is coupled to and slidably disposed on the exterior of said lumen;
moving said integrated wound closure mechanism from a stowed position to a distal deployment position, said integrated wound closure mechanism being located radially around at least a portion of said lumen.

14. The method of claim 13, further comprising advancing said integrated wound closure mechanism and an integrated wound closure component that comprises at least two elongated tissue-piercing members.

15. The method of claim 14, wherein said tissue-piercing members comprise spikes.

16. The method of claim 14, wherein said integrated wound closure component is provided with spikes which pierce the vessel wall and wherein when said integrated wound closure component is moved from a stowed position to a distal deployment position, a deforming step comprises urging said spikes toward each other.

17. The method of claim 14, wherein said integrated wound closure component has longitudinally extending legs which comprise at least two elongated tissue-piercing members and wherein when said integrated wound closure component is moved from a stowed position to a distal deployment position opposing legs of the wound closure component are directed inwardly towards one another.

18. The method of claim 13, further comprising before moving said integrated wound closure mechanism from a stowed position to a distal deployment position:
performing an interventional procedure through said lumen.

19. A method for sealing a puncture in a vessel wall comprising:
providing an apparatus comprising a housing having at least one lumen, an integrated wound closure mechanism, and an integrated annularly-shaped wound closure component that includes at least two elongated tissue-piercing members, said integrated wound closure mechanism cooperating with said at least one lumen, said housing comprising a bleedback lumen coupled with a bleedback tube extending proximally from said housing towards a proximal end of said apparatus, said bleedback tube being movable with said housing;
advancing said housing, with said bleedback tube, distally along said apparatus to advance said lumen into a vessel through a vascular puncture wherein when said integrated wound closure mechanism is slidably disposed on and exterior to said lumen, said integrated wound closure component being located radially around at least a portion of said lumen;
moving said integrated wound closure mechanism from a stowed position to a distal deployment position; and
directing tissue near the puncture in said vessel together to prevent liquid flowing through the puncture following healing of the puncture.

20. The method of claim 19, wherein said integrated wound closure component comprises at least two elongated tissue-piercing members.

21. The method of claim 20, wherein said tissue-piercing members comprise spikes.

22. The method of claim 19, wherein said integrated wound closure component is provided with spikes which pierce the vessel wall and wherein when said integrated wound closure component is moved from a stowed position to a distal deployment position, a deforming step comprises urging said spikes toward each other.

23. The method of claim 19, wherein said integrated wound closure component has longitudinally extending legs which comprise at least two elongated tissue-piercing members and wherein when said integrated wound closure component is moved from a stowed position to a distal deployment position opposing legs of the wound closure component are directed inwardly towards one another.

24. The method of claim 19, further comprising before moving said integrated wound closure mechanism from a stowed position to a distal deployment position:
  performing an interventional procedure through said lumen.

\* \* \* \* \*